(12) United States Patent
Zemp

(10) Patent No.: US 12,396,706 B2
(45) Date of Patent: Aug. 26, 2025

(54) SYNTHETIC PHASE ALTERNATING ROW-COLUMN TRANSDUCER ARRAY

(71) Applicant: Roger Zemp, Edmonton (CA)

(72) Inventor: Roger Zemp, Edmonton (CA)

(73) Assignee: CLINISONIX INC., Edmonton (CA)

( * ) Notice: Subject to any disclaimer, the term of this patent is extended or adjusted under 35 U.S.C. 154(b) by 113 days.

(21) Appl. No.: 18/376,739

(22) Filed: Oct. 4, 2023

(65) Prior Publication Data

US 2025/0114070 A1    Apr. 10, 2025

(51) Int. Cl.
*A61B 8/00* (2006.01)
*B06B 1/02* (2006.01)
*B06B 1/06* (2006.01)

(52) U.S. Cl.
CPC .............. *A61B 8/4488* (2013.01); *A61B 8/54* (2013.01); *B06B 1/0215* (2013.01); *B06B 1/0292* (2013.01); *B06B 1/0622* (2013.01); *B06B 2201/51* (2013.01); *B06B 2201/55* (2013.01); *B06B 2201/57* (2013.01); *B06B 2201/76* (2013.01)

(58) Field of Classification Search
CPC ... A61B 8/4483; A61B 8/4488; A61B 8/4494; A61B 8/483; A61B 8/488; A61B 8/5207; A61B 8/54; B06B 1/0215; B06B 1/0292; B06B 1/0622; B06B 2201/51; B06B 2201/55; B06B 2201/57; B06B 2201/76
See application file for complete search history.

(56) References Cited

U.S. PATENT DOCUMENTS

| | | | |
|---|---|---|---|
| 4,425,525 A | 1/1984 | Smith et al. |
| 4,448,075 A | 5/1984 | Takemura |
| 4,580,451 A | 4/1986 | Miwa |
| 4,671,293 A | 6/1987 | Shaulov |
| 5,027,820 A | 7/1991 | Pesque |
| 5,152,294 A | 10/1992 | Mochizuki |

(Continued)

FOREIGN PATENT DOCUMENTS

WO    2008/033528 A3    3/2008

OTHER PUBLICATIONS

Rasmussen, M. F., & Jensen, J. A.; 3-D ultrasound imaging performance of a row-col. addressed 2-D array transducer: A measurement study; IEEE International Ultrasonics Symposium (IUS); 2013, July; pp. 1460-1463.

(Continued)

*Primary Examiner* — Mark D Remaly
(74) *Attorney, Agent, or Firm* — Nathan V. Woodruff

(57) ABSTRACT

An ultrasound array system has an array of transducer elements made from bias-sensitive material, each transducer element comprising at least a first sub-element and a second sub-element. A series of column electrodes is patterned in columns on a first surface of the array of transducer elements. A series of row electrodes is patterned in rows on a second surface of the array. The rows are at an angle relative to the columns, wherein, for each transducer element, the first sub-element and the second sub-element are connected to different row electrodes. A controller is connected to selectively apply voltage signals to the series of column electrodes and the series of row electrodes. The controller is programmed to apply a first voltage signal to the first sub-element and a second voltage signal to the second sub-element that is distinct from the first voltage signal.

16 Claims, 23 Drawing Sheets

(56) References Cited

U.S. PATENT DOCUMENTS

| | | | |
|---|---|---|---|
| 5,327,895 | A | 7/1994 | Hashimoto |
| 5,345,139 | A | 9/1994 | Gururaja |
| 5,410,205 | A | 4/1995 | Gururaja |
| 5,460,179 | A | 10/1995 | Okunuki |
| 5,460,181 | A | 10/1995 | Seyed-Bolorforosh |
| 5,488,956 | A | 2/1996 | Bartelt |
| 5,490,512 | A | 2/1996 | Kwon et al. |
| 5,657,295 | A | 8/1997 | Howard |
| 5,671,746 | A | 9/1997 | Dreschel |
| 5,846,201 | A | 12/1998 | Adams |
| 6,381,197 | B1 | 4/2002 | Savord |
| 6,419,633 | B1 | 7/2002 | Robinson |
| 7,087,023 | B2 | 8/2006 | Daft |
| 7,544,165 | B2 | 6/2009 | Mamayek |
| 7,618,373 | B2 | 11/2009 | Ladabaum |
| 7,780,597 | B2 | 8/2010 | Panda |
| 9,285,466 | B2 | 3/2016 | Gomersall |
| 2005/0043624 | A1 | 2/2005 | Oliver |
| 2007/0079658 | A1 | 4/2007 | Wagner |
| 2007/0206193 | A1 | 9/2007 | Pesach |
| 2009/0079299 | A1 | 3/2009 | Bradley et al. |
| 2009/0112095 | A1 | 4/2009 | Daigle |
| 2009/0299184 | A1 | 12/2009 | Walker et al. |
| 2010/0239133 | A1 | 9/2010 | Schmitt et al. |
| 2011/0054292 | A1 | 3/2011 | Hirson |
| 2014/0117809 | A1 | 5/2014 | Zemp |
| 2017/0337682 | A1 | 11/2017 | Liao et al. |
| 2018/0146949 | A1 | 5/2018 | Nakamura |
| 2018/0164418 | A1 | 6/2018 | Zemp |
| 2019/0216421 | A1 | 7/2019 | Hamilton et al. |
| 2019/0235077 | A1 | 8/2019 | Zemp et al. |
| 2020/0041644 | A1 | 2/2020 | Brown et al. |
| 2020/0305840 | A1 | 10/2020 | Sboros et al. |
| 2021/0302575 | A1 | 9/2021 | Iwama |
| 2023/0075328 | A1 | 3/2023 | Zemp et al. |
| 2023/0083086 | A1 | 3/2023 | Zemp |

OTHER PUBLICATIONS

Sampaleanu, A., Zhang, P., Kshirsagar, A., Moussa, W., & Zemp, R. J.; Top-orthogonal-to-bottom-electrode (TOBE) CMUT arrays for 3-D ultrasound imaging; IEEE transactions on ultrasonics, ferroelectrics, and frequency control; 2014; 61(2); pp. 266-276.

Wang, Y., Guo, Z., Wang, L. V., Erpelding, T. N., Jankovic, L., Robert, J. L., & David, G.; In vivo three-dimensional photoacoustic imaging based on a clinical matrix array ultrasound probe; Journal of Biomedical Optics; 2012; 17(6); p. 061208.

Ephrat, P., Keenlislide, L., Seabrook, A., Prato, F. S., & Carson, J. J.; Three-dimensional photoacoustic imaging by sparse-array detection and iterative image reconstruction; Journal of Biomedical Optics; 2008; 13(5); p. 054052.

Chee, R. K., Sampaleanu, A., Rishi, D., & Zemp, R. J.; Top orthogonal to bottom electrode (TOBE) 2-D CMUT arrays for 3-D photoacoustic imaging; IEEE transactions on ultrasonics, ferroelectrics, and frequency control; 2014; 61(8); pp. 1393-1395.

C. Ceroici et al., "3D photoacoustic imaging using Hadamard-bias encoding with a crossed electrode relaxor array," Opt. Lett., vol. 43, No. 14, pp. 3425-3428, 2018.

K. Latham, C. Ceroici, C. A. Samson, R. J. Zemp, and J. A. Brown, "Simultaneous azimuth and Fresnel elevation compounding: A fast 3-D imaging technique for crossed-electrode arrays," IEEE Trans. Ultrason., Ferroelectr., Freq. Control, vol. 65, No. 9, pp. 1657-1668, Jun. 2018.

C. Ceroici, T. Harrison, and R. J. Zemp, "Fast orthogonal row-column electronic scanning with top-orthogonal-to-bottom electrode arrays," IEEE Trans. Ultrason., Ferroelectr., Freq. Control, vol. 64, No. 6, pp. 1009-1014, Jun. 2017.

C. Ceroici, K. Latham, B. A. Greenlay, J. A. Brown, and R. J. Zemp, "Fast orthogonal row-column electronic scanning experiments and comparisons," IEEE Trans. Ultrason., Ferroelectr., Freq. Control, vol. 66, No. 6, pp. 1093-1101, Jun. 2019.

C. Ceroici, K. Latham, R. Chee, J. A. Brown, and R. J. Zemp, "Bias-sensitive crossed-electrode relaxor 2D arrays for 3D photoacoustic imaging," Proc. SPIE, vol. 10494, Feb. 2018, Art. No. 1049420.

Seo, Chi Hyung and Jesse T. Yen. "A 256 x 256 2-D array transducer with row-col. addressing for 3-D rectilinear imaging." IEEE transactions on ultrasonics, ferroelectrics, and frequency control 56, No. 4 (2009): 837-847.

Novell, Anthony, Mathieu Legros, Jean-Marc Gregoire, Paul A. Dayton, and Ayache Bouakaz. "Evaluation of bias voltage modulation sequence for nonlinear contrast agent imaging using a capacitive micromachined ultrasonic transducer array." Physics in Medicine & Biology 59, No. 17 (2014): 4879.

bit sequence 1 1 1 0 0 ... 0
into controller 1 1 1 0 0 ... 0

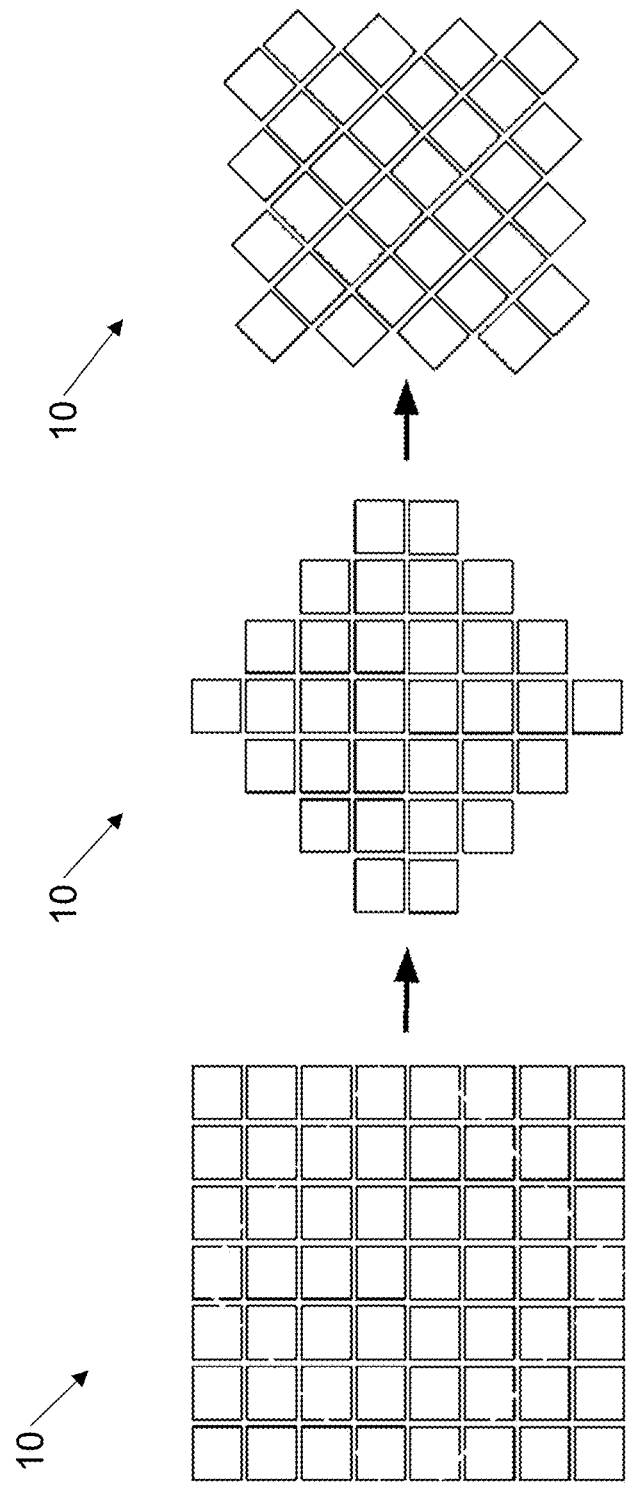

SYNTHETIC PHASE ALTERNATING ROW-COLUMN TRANSDUCER ARRAY

TECHNICAL FIELD

This relates to a transducer array and a method of imaging using the transducer array.

BACKGROUND

Two-dimensional array transducers have enabled 3D ultrasound imaging but their use in clinical settings has been limited in part by the image quality. With such 2D arrays, there exist difficult engineering trade-offs between system complexity and achievable image quality. Large probes with high-element density may be used to produce high-quality images but with a resulting large number of channels leading to significant interconnect and channel count difficulties. Implementation of fully-wired arrays is practically prohibitive, with commercial arrays available with only 32×32 elements, leading to small aperture sizes and poor image quality. Various old 3D imaging techniques have been implemented using a mechanically sweeping a linear or annular transducer but not capable of fast volumetric imaging. A few approaches have been made to reduce the channel count while having a larger aperture size, such as multiplexing and sparsely distributing the active elements with limited channels but have thus far demonstrated sidelobe artifacts that degrade image quality. Image quality from 2D arrays has been dramatically improved with the use of micro-beamforming, involving pre-amplifiers, analog-to-digital converters, and delay-and-sum circuitry implemented as a custom integrated circuit beneath the shadow of each element.

In microbeamforming, fine delays are introduced to elements before summing in groups, and coarse delays are implemented in the mainframe. Often, micro-beamformers implement tilt-only fine-delays as a linear approximation to a quadratic delay profile. These approximations can be a source of image quality degradation, especially when using parallel beamforming to reconstruct a group of adjacent A-scan lines over a wide area, as ideal focal delays are accurate only for one line-of-sight. As a result, microbeamformer-based MATRIX probes may not necessarily provide the B-scan image quality otherwise found with simpler linear or phased array probes.

Beyond image quality considerations, such microbeamforming-based MATRIX probes do not yet provide ultrafast imaging capabilities, which may offer imaging at thousands of frames per second and enable ultrasensitive blood-flow tracking, shear-wave imaging, super-resolution imaging, and other emerging applications.

Row-column arrays have been investigated as a means of reducing interconnect complexity as they can be addressed using only row and column electrodes, also known as first orthogonal to second electrode (TOBE) arrays. They have been implemented with piezoelectrics, capacitive micromachined ultrasound transducers, and more recently electrostrictive realizations. Unlike piezoelectric implementations, CMUT- and electrostrictive implementations of TOBE arrays offer bias-sensitivity, which may be used for novel imaging schemes such as Simultaneous Azimuthal and Fresnel Elevational (SAFE) compounding, which exploits Fresnel-lens-based elevational focusing. It is possible to address each element of such a bias-sensitive TOBE array by biasing a row and transmitting or receiving from a column. Hadamard or S-Matrix-encoded biasing schemes have furthermore been proposed to improve signal-to-noise ratio with good success, including in recent demonstrations of 3D imaging techniques.

Such Hadamard-encoding schemes, or invertible matrix schemes, have also been put to use for aperture-encoded synthetic aperture imaging using a recently developed imaging scheme called Fast Orthogonal Row-Column Electronic Scanning (FORCES). FORCES involves biasing columns with a sequence of Hadamard biasing patterns while transmitting pulses along rows with focal delays to create a cylindrical elevational transmit focus. By using a new Hadamard pattern for each of N transmit events, while receiving echoes from columns, an encoded synthetic transmit aperture dataset is collected. After decoding by multiplying by an inverse Hadamard matrix, the decoded channel dataset represents a synthetic transmit aperture dataset, consisting of a received signal from each element for each respective (elevationally focused) transmitting column. FORCES has been demonstrated to produce elevationally steerable B-scans with image quality superior to previous non-encoded row-column imaging schemes and significantly superior to Explososcan schemes (parallel processing techniques for high-speed ultrasound imaging with linear phased arrays) constrained by a similar total channel count. FORCES permits the use of a bias-switchable row-column array to achieve B-scan image quality that may be comparable to a linear array.

Piezoelectric, Electrostrictive and Dielectric Materials

The forward piezoelectric effect involves material strain upon applying an electric field, usually from applying a voltage between a first and second electrode. The inverse effect involves creation of voltages upon application of a force. These effects are due to molecular asymmetries and require polarized domains in the material. These domains are polarized via a poling process with high voltages and high temperatures. When the material cools, residual polarization results in the piezoelectric behavior with strains and voltages roughly linearly proportional. Piezoelectric materials exhibit both a forward and inverse piezoelectric effect.

Electrostrictive materials, in contrast have no inverse piezoelectric effect, that is, unless there is an applied bias voltage. Electrostriction is a property of all dielectric materials and is caused by displacement of ions in the crystal lattice upon being exposed to an external electric field. Positive ions will be displaced in the direction of the field, while negative ions will be displaced in the opposite direction. This displacement will accumulate throughout the bulk material and result in an overall strain (elongation) in the direction of the field. The thickness will be reduced in the orthogonal directions characterized by Poisson's Ratio (the ratio of the change in the width per unit width of a material, to the change in its length per unit length, as a result of strain). Insulating materials that consist of more than one type of atom will be ionic to some extent due to the difference of electronegativity of the atoms, and therefore exhibit electrostriction.

The resulting strain (ratio of deformation to the original dimension) is proportional to the square of the polarization. Reversal of the electric field does not reverse the direction of the deformation.

The related piezoelectric effect occurs only in a particular class of dielectrics. Electrostriction applies to all crystal symmetries, while the piezoelectric effect only applies to the 20 piezoelectric point groups of the crystal structure. Electrostriction is a quadratic effect, unlike piezoelectricity, which is a linear effect.

Ferroelectrics have a spontaneous but reversible polarization. Piezoelectric materials are ferroelectrics and may require poling to be piezoelectric without any applied bias voltage. Relaxor ferroelectrics are ferroelectric materials that exhibit high electrostriction.

TOBE Arrays for Ultrasound Imaging

Bias-switchable "first-orthogonal-to-second" (TOBE) 2D arrays may be used for 3D ultrasound and photoacoustic imaging. An example is shown in FIG. 1, which may also be referred to as a row-column array. Referring to FIG. 1, the depicted example of ultrasonic transducer array 10 includes second electrodes 12, a bias-sensitive ultrasonic layer 14, and first electrodes 16. Layers 12, 14, 16 may be used to generate and receive ultrasonic signals that are then used to produce an image of a sample. While electrodes 12 and 16 are shown and described as being generally orthogonal herein, it will be understood that they may be at other angles that still permit the transmission and reception of ultrasonic signals. Other layers may also be present, such as an insulation layer 18 to insulate the patient from electrical signals and/or heat generated by array 10, a matching layer 20 used to improve the coupling of ultrasonic signals to the sample and a shielding layer 22 used to shield the patient from electrical signals. In one example, shielding layer 22 may be a thin grounded conducting layer sandwiched between two matching layers with the objective of reducing the coupled leakage currents while minimizing or avoiding any adverse effects on the operation of array 10. The particular design of array 10 may vary depending on the implementation from what is depicted in FIG. 1. For example, some layers may not be present, and other layers may be included beyond those depicted that perform the same or different functions such one or more acoustically absorbing backing layer, or the number of layers may be reduced by incorporating more than one function into one or more layers. For example, dielectric layer 14 may be a composite of multiple layers or materials that may improve the functionality of array 10, as is known in the art. In addition, while orthogonality is convenient in designing such an array, it is not a necessary condition, provided that the first and second electrodes are crossed, or angled, sufficiently to permit individual elements to be separately addressed. Rather than requiring every element to be addressed as in a fully wired array, TOBE arrays operate by addressing only rows and columns. Unlike piezoelectric materials, CMUTs- and electrostrictive-relaxor based crossed electrode arrays allow important additional control and multiplexing by using bias voltages as discussed below. Electrostrictive-relaxor crossed electrode arrays become piezoelectric upon the application of a bias voltage, and the polarity of the material depends on the polarity of the bias voltage. This unique property allows unique bias-controlled readout of row-column electrostrictive arrays. In particular, the response to an excitation with a positive bias may be the same as that of an amplitude-inverted excitation with a negative bias. Likewise, the received signal due to a pressure transient &p received with a positive bias voltage may be effectively polarity (or pulse) inverted with a negative bias voltage.

Key ultrasound imaging schemes have been demonstrated with TOBE arrays. One of the original imaging schemes is row-column scanning (which may be referred to as Scheme 1, shown in FIG. 2A). This involves one-way elevational transmit focusing along rows and one-way receive azimuthal focusing along columns and can be implemented without any bias encoding. The advantage of this approach is that it can achieve volumetric imaging very quickly (with ~N transmits for an N×N array), but the disadvantage is clutter due to lack of two-way focusing. Next synthetic aperture-based scanning may be introduced using bias encoding. By biasing a column and transmitting on a row, only the intersecting element produced appreciable transmit/receive sensitivity. Thus, by addressing only rows and columns, single element control may be achieved. More complicated imaging schemes could be implemented using superposition principles. This may include Simultaneous Azimuthal and Fresnel Elevation (SAFE) compounding, which produced high-quality 3D scans, but requires significant coherent compounding.

Additionally, Fast Orthogonal Row-Column Electronic Scanning (FORCES) May be introduced, as shown in FIG. 2B, which achieves excellent B-mode image quality with high SNR and ideal in-plane two-way synthetic aperture focusing with flexible electronic steering capacity. FORCES involves elevational transmit focusing by transmitting on rows, while biasing columns with a bias pattern selected from columns of a Hadamard Matrix. FORCES allows two-way azimuthal focusing, and adjustable elevational focusing. After N transmit events, each using a unique Hadamard vector, the channel data from columns is decoded using an inverse Hadamard Matrix to recover an effective synthetic aperture dataset for two-way in-plane focusing but only one-way elevational transmit focusing. Importantly, the Hadamard aperture encoding enables a $\sqrt{N}$ SNR enhancement compared to synthetic aperture imaging when activating only a single column at a time. FORCES may be used to achieve an image quality that is superior to both an industry standard Explososcan method, and Scheme 1 in simulations of a cyst phantom, shown in FIG. 3A. It was also demonstrated experimentally by imaging a rat heart, shown in FIG. 3B.

The FORCES imaging scheme is described in U.S. Pat. No. 6,224,382 (Ceroici et al.), entitled "Fast Orthogonal Row-Column Electronic Scanning" and the Hadamard-encoded readout from a TOBE array is described in U.S. pregrant publication no. 2019/0235077 (Ceroici et al.), entitled "3d Imaging Using a Bias-Sensitive Crossed-Electrode Array", and the contents of each patent document are incorporated herein by reference.

SUMMARY

According to an aspect, there is provided an ultrasound array system, comprising an array of transducer elements made from bias-sensitive material, each transducer element comprising at least a first sub-element and a second sub-element; a series of column electrodes patterned in columns on a first surface of the array of transducer elements; a series of row electrodes patterned in rows on a second surface of the array, the rows being at an angle relative to the columns, wherein, for each transducer element, the first sub-element and the second sub-element are connected to different row electrodes; and a controller connected to selectively apply voltage signals to the series of column electrodes and the series of row electrodes, wherein the controller is programmed to apply a first voltage signal to the first sub-element and a second voltage signal to the second sub-element that is distinct from the first voltage signal.

According to another aspect, the ultrasound array system may comprise one or more of the following features, alone or in combination: the first sub-element and the second sub-element may be connected to different columns; the controller may further comprise receiving electronics and a processor for reconstructing images; the transducer elements may comprise bias-sensitive ultrasonic elements that comprise electrostrictive material, relaxor ferroelectric material, piezoelectric material, capacitive micromachined ultrasound transducers, or combinations thereof; the array may further comprises a backing layer, one or more matching layers, an acoustic lens, an interposing layer, an electromagnetic shielding layer, or combinations thereof; the controller may comprise driving circuits and biasing circuits connected to the series of row electrodes, the series of column electrodes, or the series of row electrodes and the series of column electrodes; the controller may apply a first driving signal to a plurality of first sub-elements and a second driving signal to a plurality of second sub-elements, the first driving signal being separated from the second driving signal by a phase shift or delay; the first driving signal may be out of phase with the second driving signal by between 85 and 95 degrees; the controller may be programmed to interchange a bias voltage and a driving signal between the series of column electrodes and the series of row electrodes after an initial transmit event; the controller may be programmed to apply a first bias voltage pattern for a transmit event and a second bias voltage pattern for a receive event immediately following the transmit event; the controller may comprise biasing electronics that comprise programmable levels, high-voltage transistors, digital to analog converters, programmable variable resistors, DC-to-DC converters, pulse-wave modulation electronics, or combinations thereof; the controller may comprise one or more GPU, one or more CPU, one or more FPGA, one or more ASIC, or combination thereof; there may be a housing having a form factor that is planar, concave, convex, plano-concave, plano-convex, biconcave, handheld, wearable, trans-esophageal, transrectal, transvaginal, endoscopic or laparoscopic; the controller may be configured to implement one or more of the following imaging methods: FORCES, uFORCES, Hadamard-Encoded reception, Hadamard-Encoded X-Power Doppler, or SAFE compounding imaging; the pitch between elements may be less than twice an acoustic wavelength of a center frequency of the array of transducer elements; and the sub-elements may have different resonance frequencies such that the array of transducer elements comprises interlaced high- and low-frequency transducer elements.

According to an aspect, there is provided a method of driving an ultrasonic array, comprising the steps of: providing an array of transducer elements made from bias-sensitive material, each transducer element comprising at least a first sub-element and a second sub-element, a series of column electrodes patterned in columns on a first surface of the array of transducer elements, and a series of row electrodes patterned in rows on a second surface of the array, the rows being at an angle relative to the columns, wherein, for each transducer element, the first sub-element and the second sub-element are connected to different row electrodes; applying a first biasing pattern to the row electrodes connected to a plurality of first sub-elements and applying a driving signal to the column electrodes connected to the plurality of first sub-elements; and applying a second biasing pattern to the row electrodes connected to a plurality of second sub-elements.

According to an aspect, the method may comprise one or more of the following elements, alone or in combination: a return signal may be received on the column electrodes connected to the plurality of second sub-elements as a receive event; the first biasing pattern may be selected to achieve a net desired phase when acoustic emissions from adjacent elements combine after diffraction; there may be a plurality of transmit events and a plurality of receive events; the plurality of receive events may comprise a series of bias voltage changes in time to implement dynamic receive focusing; coherent compounding may be applied over the plurality of transmit events and the plurality of receive event; a second driving signal may be applied to the column electrodes connected to the plurality of second sub-elements, the second driving signal being between 85 and 95 degrees out of phase from the first driving signal; a parabolic phase or delay may be applied to the column electrodes to implement azimuthal focusing; a parabolic phase or Frensel Lens may be applied to the row of elements to implement elevational focusing; the first biasing pattern, the driving signal, and the second biasing patter may be selected to implement 3D steerable continuous wave Doppler ultrasound, Pulse-Wave Doppler Ultrasound, Acoustic Radiation Force Impulse Imaging, high-intensity focused ultrasound, histotripsy, ultrasound-aided drug delivery, or ultrasound-aided biomarker liberation; the first biasing pattern and the second biasing pattern may be selected to implement an elevationally-focusing phase function or Fresnel Lens; signals may be received on the column electrodes connected to the plurality of first sub-elements and the column electrodes connected to the plurality of second sub-elements, wherein a phase shift of between 85-95 degrees is applied to signals received on the column electrodes connected to the plurality of second sub-elements and then additively combined; the phase shift may be applied using analog circuits, digital circuits, or with software; at least one of the first biasing pattern, the second biasing pattern, and the driving signal may comprise pulse-inversion or amplitude modulation for harmonic imaging, and wherein a quadratic phase focusing profile may be specific to at least a second harmonic of a fundamental driving frequency of the driving signal; the method may further comprise one or more acoustic emission sources, the one or more acoustic emission sources may comprise an ultrasonic emission source, a photoacoustic emission source, a thermoacoustic emission source, or combinations thereof; the sub-elements may have different resonance frequencies such that the array of transducer elements comprises interlaced high- and low-frequency transducer elements, and further comprising the steps of injecting microbubble contrast agents, transmitting with a low-frequency signal, and receiving a high-frequency signal to detect harmonics or super-harmonics for contrast agent imaging; applying at least one of the first biasing pattern an the second biasing pattern may comprise applying a sequence of bias voltage patterns derived from an invertible matrix.

According to an aspect, there is provided a bias-sensitive synthetic phase alternating row-column (SPARC) ultrasound array system comprising a multiplicity of bias-sensitive ultrasound transducer elements, each element comprised of at least two sub-elements. Top electrode strips patterned in columns that connect to a subset of transducer sub-elements within each element in the column of elements. Each element is addressed by two or more such column electrodes, each column electrode connecting to at least one but fewer than all the sub-elements in an element. Bottom electrode strips are patterned in rows which are connected to elements or subsets of transducer sub-elements. Adjacent row electrodes are not connected to the same sub-elements or column electrodes. Biasing electronics are connected to at least one row or one column. A controller controls a biasing voltage and signal applied to each row and column.

According to another aspect, there is provided an architecture for a row-column 2D transducer array comprising bias-sensitive transducer elements, where each element is addressed with two or more row electrodes and/or two or more column electrodes, each connecting to sub-elements, and with adjacent row electrodes not connected to the same sub-elements or column electrodes. This architecture coupled with arbitrary-voltage biasing electronics will enable a desired phase to be synthesized on transmit or receive along each element in a column of elements. The architecture may be used in multi-frequency row-column arrays, 3D beam steering, and a form of dynamic receive beamforming in 3D, and may be implemented without requiring specialized electronics on the array.

According to an aspect, there is provided an architecture for a bias-sensitive row-column array comprising elements in rows and columns. Each element comprises first and second bias-sensitive sub-elements. Each element is addressed by first and second rows and first and second columns. The sub-elements or the row-column routing are positioned in a way that every other sub-element along a row pair is connected in an alternating pattern and every other sub-element along a column pair is connected to the column electrodes in an alternating pattern.

Methods discussed herein may provide electronic elevational focusing control, electronic scan-plane steering, and 3D imaging.

In other aspects, the features described above may be combined together in any reasonable combination as will be recognized by those skilled in the art.

BRIEF DESCRIPTION OF THE DRAWINGS

These and other features will become more apparent from the following description in which reference is made to the appended drawings, the drawings are for the purposes of illustration only and are not intended to be in any way limiting, wherein:

FIGS. 19A, 19B, and 19C depicts how a SPARC array may be set up in Field II.

DETAILED DESCRIPTION OF PREFERRED EMBODIMENTS

Figure 1:
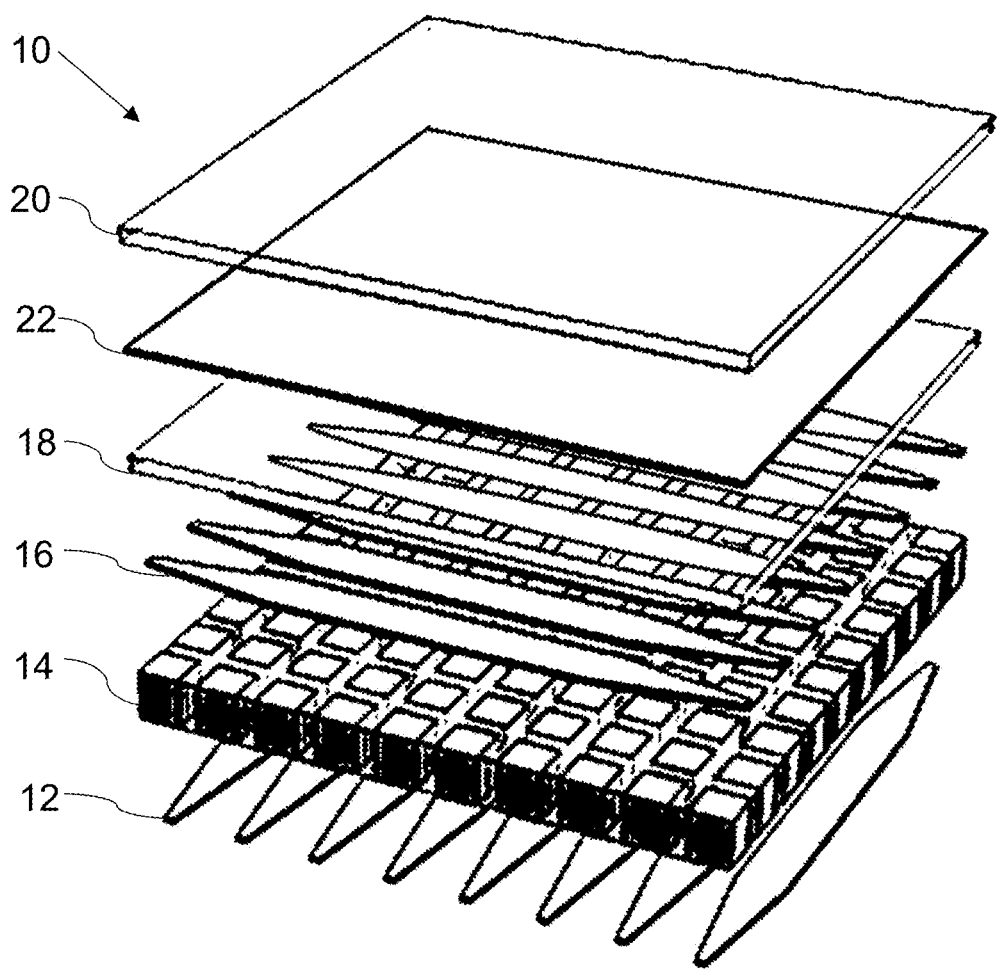
FIG. 1 is an exploded perspective view of a bias-switchable row-column array.
Figure 2A:
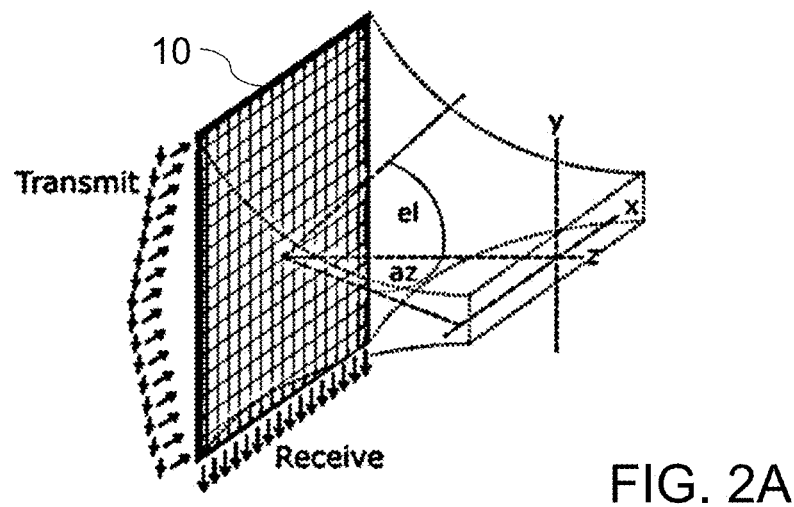
FIG. 2A is a diagram of a Scheme 1 imaging method, which does not require the row-column array to be bias switchable.
Figure 2B:
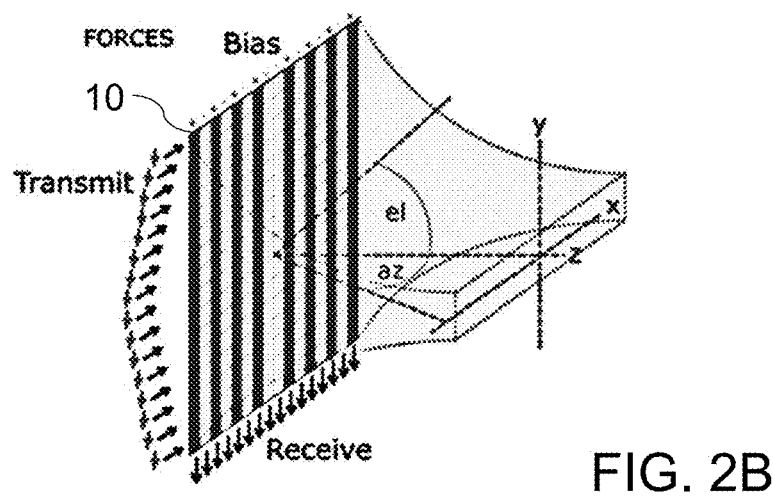
FIG. 2B is a diagram of a Fast Orthogonal Row-Column Electronic Scanning (FORCES) imaging scheme using a TOBE array, which biases columns while pulsing on rows and receiving on columns.
Figure 3A:
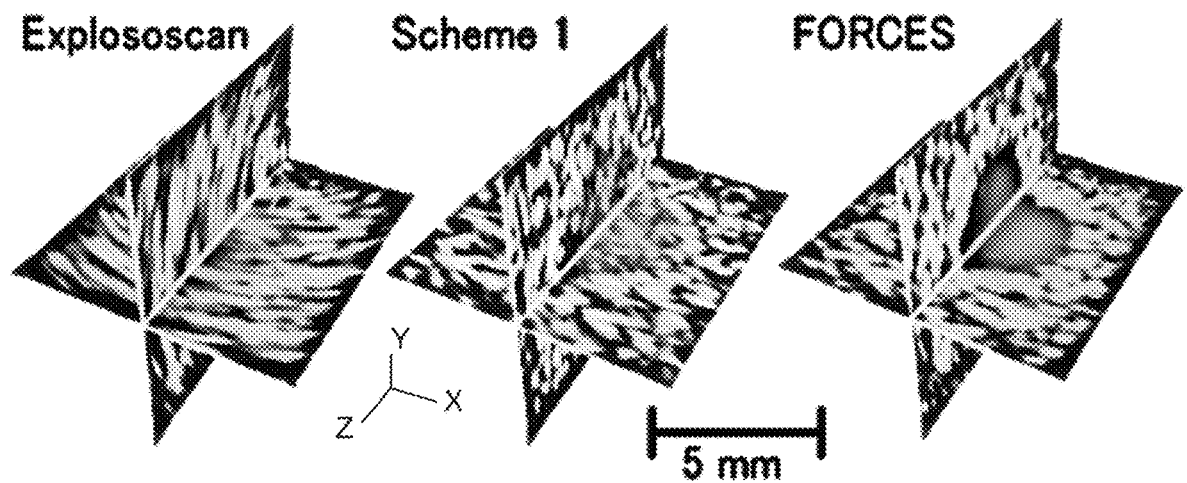
FIG. 3A is a comparison of images obtained from FORCES, Explososcan, and Scheme 1 imaging schemes for phantom imaging.
Figure 3B:
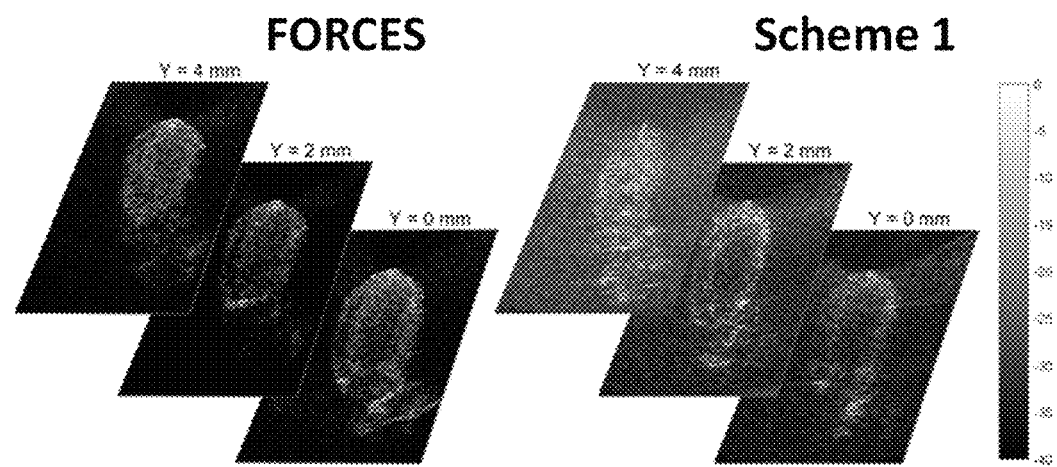
FIG. 3B is a comparison of images obtained from FORCES, Explososcan, and Scheme 1 imaging schemes for imaging a rat heart.
Figure 4:
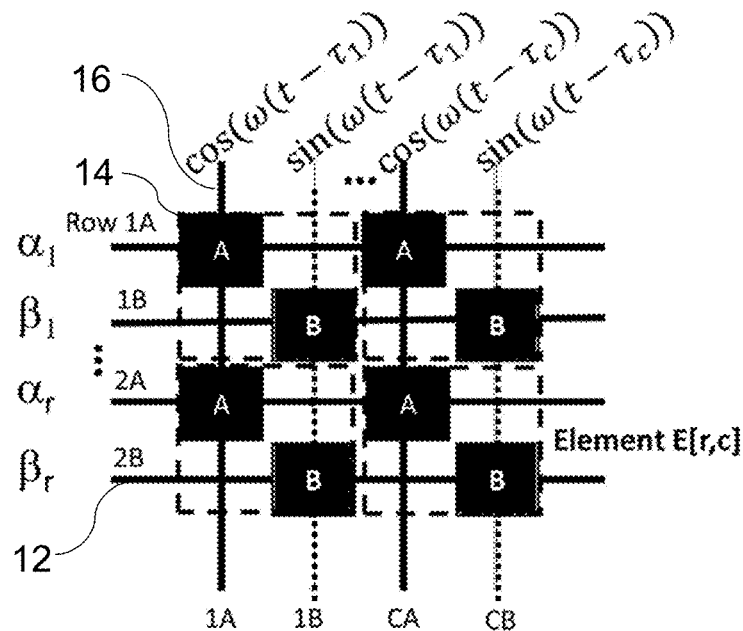
FIG. 4 is an illustration of a SPARC array architecture and the use of bias voltage levels to create a transmit signal.

Referring to FIG. 4, an architecture for a bias-sensitive row-column array 10 is shown. The array 10 has elements 14 in rows and columns, with each element 14 made up of bias-sensitive sub-elements, for example A and B. In the depicted example, each element 14 is addressed by two rows 12 and two columns 16, but in general each element should be addressed by more than only one row 12 or only one column 16. The sub-elements A and B, or the row-column routing, is positioned in a way such that every other sub-element along a row pair is connected in an alternating pattern. Likewise, in this embodiment, every other sub-element along a column pair is connected to the column electrodes in an alternating pattern. It will be understood that this design of elements with sub elements may also be implemented using appropriate control algorithms based on a typical TOBE array.

The array 10, including the sub-elements and the electrodes, may be manufactured using lithography, scratch dicing, or laser micromachining. Elements 14 or sub-elements A, B within the array 10 may be fabricated such that they have different resonance frequencies to enable a multi-frequency array with interlaced high- and low-frequency elements. This may be used in conjunction with the delays and bias differences between sub-elements as discussed below to enhance an imaging method.

This design allows for new capabilities for row-column arrays. In some examples, the design may be used in multi-frequency row-column arrays, such as with sub-elements with different resonant frequencies, to enable different transmit and receive biasing patterns, and/or faster readout. In addition, the design may also enable each element in a column to achieve a desired phase shift when transmitting or receiving, which permits a focused ultrasound beam that is steerable in 3D and may also be used to achieve some degree of dynamic-receive beamforming without an ASIC. In some cases, the array may be controlled to transmit along columns and receive along the rows, which may involve the use of a different biasing pattern.

The array 10 uses electrostrictive materials, which exhibit strains that are quadratic with applied voltages. In tensor notation, a strain can be modelled as $\epsilon_{ij}=Q_{ijkl}D_K D_l$, where $Q_{ijkl}$ is the electrostriction tensor, and $D_k$ are components of the electric displacement field, equal to the sum of applied electric field and residual polarization: $D_k=\epsilon E_k+P_k$.
More generally, the displacement field may be viewed as a component of the electric field that changes quickly, and a component associated with a slower polarization response. This may be written as:

$$D(t) = \varepsilon_0[\varepsilon_\infty E(t) + \Phi(t) * E(t)],$$

where $\Phi(t)=(\varepsilon_r-\varepsilon_\infty)[1-\phi(t)]$, * is temporal convolution, $\phi(t)=P(t)/P(0)$, and $\varepsilon_r$ and $\varepsilon_\infty$ are the low- and high-frequency limits of relative dielectric permittivity. The complex frequency-dependent permittivity is related to $\phi$ as:

$$\frac{\varepsilon^*(\omega) - \varepsilon_\infty}{\varepsilon_r - \varepsilon_\infty} = \mathcal{L}\left\{-\frac{d}{dt}\phi(t)\right\},$$

where $\mathcal{L}$ is the Laplace Transform operator. The Debye model for $\phi$ is a decaying exponential:

$$\phi(t) = e^{-\frac{t}{\tau_m}} u(t)$$

where u(t) is a step function and where $\tau_m$ is the characteristic relaxation time. Many other more complex phenomenological models of relaxation have also been proposed.

When the thickness-mode excitation axis is k=3, and electric fields are applied in this direction, the relevant strain is $\epsilon_{33} \propto Q(\varepsilon E_3+P_3)^2$, where $Q=Q_{3333}$. Dropping subscripts for convenience, the AC strain due to a transient voltage excitation $\delta E$ is $\epsilon_{AC} \propto HPF\{(\varepsilon(\delta E)+P)^2\} \propto \varepsilon P\delta E$ to first order in $\delta E$. This is the forward piezoelectric effect showing linearity with excitation voltage. Thus piezo-electricity is described here as an electrostrictive effect when there is a residual polarization present. For a purely electrostrictive non-ferroelectric material, there is no residual polarization, $P_k=0$. However, if the transducer is biased with a DC electric field $E_3$, then, again dropping subscripts: $\epsilon_{AC}=h(t)*\epsilon_{33}$ where h is the bandpass transducer electromechanical response, thus $\epsilon_{AC}=h*Q\{D(t)^2\}$. Expanding, we have $$\epsilon_{AC} = h(t) * \left(\varepsilon_0[\varepsilon_\infty E(t) + \Phi(t) * E(t)]\right)^2 Q = h(t) * \left(\varepsilon_0[\varepsilon_\infty(E + \delta E) + \Phi(t) * (E + \delta E)]\right)^2 Q = h(t) * \{\varepsilon_0^2 \varepsilon_\infty^2 (E + \delta E)^2 + 2\varepsilon_0 \varepsilon_\infty (E + \delta E)\varepsilon_\infty \Phi(t) * (E + \delta E) + \varepsilon_0^2 [\Phi(t) * (E + \delta E)]^2\} Q$$

When E(t)=E is a constant DC field, we have $$\Phi(t) * E(t) = E \int_{-\infty}^{\infty} \Phi(t) dt = -E(\varepsilon_r - \varepsilon_\infty)\int_0^\infty \dot{\phi}(t) dt = (\varepsilon_r - \varepsilon_\infty)E(\phi(0) - \phi(\infty)) = (\varepsilon_r - \varepsilon_\infty)E.$$

when the material has a large relative dielectric constant, as in our case (e.g., PMN has a giant relative permittivity of 20,000), the relative permittivity $\varepsilon_r \gg \varepsilon_\infty$ and we have that $\Phi(t)*E \approx \varepsilon_r E$.

Also, when the transducer is driven with an AC electric field $\delta E(t)$ with a frequency much higher than the relaxation-rate $1/\tau_m$, the material cannot adequately respond and $\Phi(t)*\delta E \approx 0$ (or small). Thus, $$\Phi(t) * (E + \delta E) \approx \varepsilon_r E.$$

Simplifying with these approximations:

$$\epsilon_{AC} \approx h(t) * \{\varepsilon_0^2(2E\delta E + \delta E^2) + 2\varepsilon_0 \varepsilon_\infty \delta E \varepsilon_0 \varepsilon_r E\} Q = h(t) * \{\varepsilon_0^2 \varepsilon_\infty^2(1 + \varepsilon_r/\varepsilon_\infty)2E\delta E(t) + \varepsilon_0^2 \varepsilon_\infty^2 \delta E^2(t)\} Q$$

When $\varepsilon_r \gg \varepsilon_\infty$, and when $\varepsilon_r E \gg \varepsilon_\infty \delta E$ (i.e., $\delta E/E \ll \varepsilon_r/\varepsilon_\infty$), this becomes simply $$\epsilon_{AC} \approx 2Q(\varepsilon_0^2 \varepsilon_\infty \varepsilon_r E)(h(t) * \delta E(t)) = h(t) * 2QP_I(\varepsilon_0 \varepsilon_\infty \delta E(t))$$

Here $P_I=\varepsilon_r E$ is an induced polarization, and $2QP_I$ is an effective (induced) piezoelectric coefficient.

Thus, the material behaves like a piezoelectric material with approximate linearity in driving voltage $\delta E$. Importantly, the induced polarization $\varepsilon E$ has a polarity dependent on the biasing field polarity. This leads to important properties that we require for bias-encoded imaging schemes discussed below. In particular, the response to an excitation $\delta E$ with a positive bias is the same as that of an amplitude-inverted excitation $-\delta E$ with a negative bias: $\epsilon_{33}=Q(E_3+\delta E_3)^2=Q(-E_3-\delta E_3)^2$. Also, $Q(E_3-\delta E_3)^2=Q(-E_3+\delta E_3)^2$. Likewise, measured voltage signals $\delta V \propto \delta E$ depend linearly on AC strain and bias voltage to first order. Thus, the received signal due to a pressure transient δp received with a positive bias voltage is effectively polarity inverted with a negative bias voltage. This property is used for imaging schemes with the arrays proposed herein.

In the depicted example on FIG. 4, signals are transmitted on columns, and bias voltages are applied on rows. The designation of row and column is arbitrary insofar as it implies a particular orientation of array 10. In some cases, if permitted by a given design, the role of the rows and columns may be exchanged, such that bias voltages are applied on columns, and signals are transmitted on rows after a previous image has been obtained.

The pressure emitted from element E[r,c] combined from sub-elements A and B may be defined as follows:

$$P_{rc}(t) = \alpha_r \cos(\omega(t - \tau_c)) + \beta_r \sin(\omega(t - \tau_c))$$

Then, with $$\alpha_r = \cos(\varphi_r), \beta_r = \sin(\varphi_r)$$

the pressure may be defined as $$P_{rc}(t) = \cos(\omega(t - \tau_c) + \varphi_r)$$

where $\tau_c$ represents the delays for transmit focusing along the azimuth, and $\varphi_r$ represents the programmable phase for focusing along the elevation. This is discussed in more detail below.

Synthetic Phase for Arbitrary 3D Transmit Focusing and Steering

The process described herein may be used in various applications that benefit from a method that allows the transmit and/or receive events from an ultrasound array to be steered or focused. Examples of applications may include 3D steerable continuous wave Doppler ultrasound, Pulse-Wave Doppler Ultrasound, Acoustic Radiation Force Impulse Imaging, high-intensity focused ultrasound, histotripsy, ultrasound-aided drug delivery, and ultrasound-aided biomarker liberation. As will be noted, some of these applications do not involve or require imaging, but instead are used in treatment or diagnostic methods. In those applications, a receive function may not be required. Examples of some applications are discussed below.

Continuous Wave ("CW") Transmit Operation (e.g., for CW Doppler):
Consider the trigonometric identity:

$$P \cos(\omega t + \varphi) = P \cos(\omega t)\cos(\varphi) - P \sin(\omega t)\sin(\varphi)$$

Let α=P cos(φ) and β=P sin(φ) be proportional to the bias voltages applied to row rA and row rB associated with row r of elements containing sub-elements A and B, respectively, while column cA is driven with a cosine carrier and column cB is driven with a sine carrier. Then after diffractive propagation resulting in effective summation, the net signal from the element (r,c) consisting of the two sub-elements A and B is equivalent to P cos(ωt+φ). In some examples, the bias voltages applied to rows may be designed to implement a net desired phase when acoustic emissions from adjacent elements combine after diffraction. In addition to acoustic emissions, other sources of emissions may include photoacoustic emissions or thermoacoustic emissions.

When driving multiple elements in a SPARC array to create an elevational focus centered about the array height, the rows rA and rB can be configured to produce (phase-wrapped) quadratic phase $\varphi_r$=wrap(ωτ, 2π), where τ=[$\sqrt{F^2+y_r^2}$−F]/$c_0$, and where F is the focal length, $y_r$ is the y-position of row r, and $c_0$ is the speed of sound. When elevational steering is also desired, an additional phase ramp term may be included.

If azimuthal focusing is also desired, a quadratic delay may be applied to driving waveforms applied to columns c, with the carrier phase of columns cA and cB driven with, for example, a 90-degree phase shift, or a shift that is between 85 and 95 degrees.

As such, pulse inversion or amplitude modulation may be used for harmonic imaging, and where the quadratic phase focusing profile may be specific to the second (or higher) harmonic of the fundamental driving frequency.

Long-Pulse Operation: (e.g., for pulse-wave Doppler): The above analysis may be modified by including a pulse envelope P(t) as follows:

$$P(t)\cos(\omega t)\cos(\varphi) - P(t)\sin(\omega t)\sin(\varphi) = P(t)\cos(\omega t + \varphi)$$

Note that the synthesized phase φ shows up in the resulting cosine carrier but does not result in a delay in the envelope.

Short Pulse Operation: (e.g., for imaging): The pulse should be long enough to achieve desired interference between the shortest and longest pathlengths for focusing. Pathlength differences may degrade axial resolution. This may be improved with compounding or nonlinear (e.g., Tissue Harmonic) imaging.

When compounding, one strategy is to use two or more transmit events, where the focal depth is changed between transmissions, such that the compounded received signals provides an effectively shorter pulse. This can be accomplished, for example by ensuring that there is a phase inversion or delay that cancels the two waveforms when they overlap but does not cancel them when they don't. It may be possible to simultaneously perform compounding of plane waves or diverging waves applied in the azimuthal direction.

In other words, when the transmit Fresnel aperture is generated as a set of transmit Fresnel sub-apertures, each transmit event that corresponds to a respective transmit Fresnel sub-aperture may be delayed by a respective transmit time delay selected to compensate for variations in path lengths between the transmit Fresnel sub-apertures and the focal point; and when the receive Fresnel aperture is generated as a set of receive Fresnel sub-apertures, each signal corresponding to a respective receive Fresnel sub-aperture is delayed by a time delay selected to compensate variations in path lengths between the receive Fresnel sub-apertures and the focal point, prior to adding respective signals from the receive Fresnel sub-apertures together.

Figure 5:
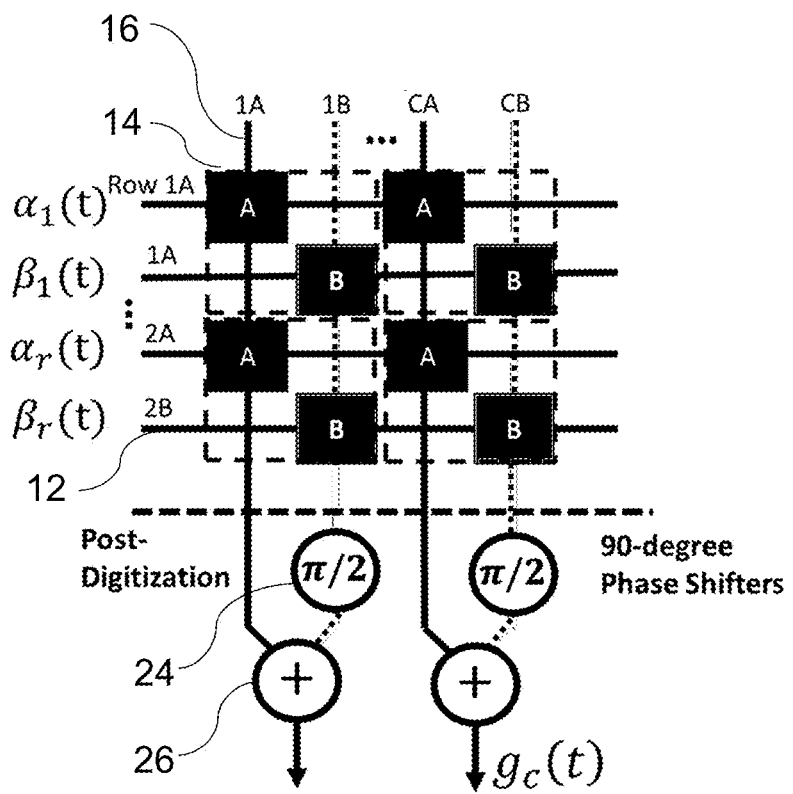
FIG. 5 is an illustration of a SPARC array used in receive focusing or steering.

Synthetic Phase for Receive Focusing in 3D: Similar comments as above may apply to receive focusing. However, instead of driving columns with waveforms which are pairwise 90-degrees out of phase, signals may be received from columns. The phase shift, such as a 90-degree phase shift (or a 85 to 95 degree shift, or about one-quarter period shift), may be implemented on every other column, or between sub-elements within each array element. This phase-shift may be implemented with an analog circuit, a digital circuit, or in software. Once shifted, the receive signals may be additively combined Referring to FIG. 5, an array is depicted that may be used to achieve (dynamic) receive focusing or steering. After a phase-shift operation 24, pairwise column data are summed in block 26. The result is a sum of acoustic signals along columns, where each element in the column is weighted by an amplitude and a phase. This assumes that the received acoustic signal on sub-elements A and B of an element are approximately equal to each other. This assumption is a reasonable approximation when the imaging targets are far relative to the size of an element and when element size is comparable to or smaller than an acoustic wavelength.

More concisely, if the pressure on element at row r and column c is $P_{rc}(t)=e_{rc}(t)\cos(\omega t+\theta_{rc}(t))$ then the summed column signal $g_c(t)$ may be modelled as:

$$g_c(t) = \sum_r \alpha_r e_{rc}(t)\cos(\omega t + \theta_{rc}) + \sum_r \beta_r e_{rc}(t)\sin(\omega t + \theta_{rc})$$

Choosing $\alpha_r=\cos(\varphi_r(t))$ and $\beta_r=-\sin(\varphi_r(t))$, the summed signal becomes:

$$g_c(t) = \sum_r e_{rc}(t)\cos(\omega t + \theta_{rc}(t) + \varphi_r(t))$$

When arbitrary-bias-voltage levels are programmed to implement a quadratic phase along columns, fixed-focus elevation-receive focusing can be achieved. When the bias voltages are dynamically changed to implement a time-varying quadratic phase along columns, dynamic receive elevation focusing may be achieved for each transmit event. In this case:

$\varphi_r(t)=\text{wrap}(\omega\Delta\tau_r)$

When there is no steering, $$\Delta\tau_r = \frac{\sqrt{y_r^2 + F_e^2(t)} - F_e(t)}{c_0}$$

and the elevational focus $F_e(t)$ is adjusted as half the round-trip time-of-flight:

$$F_e(t) = c_0 t/2$$

When steering at an elevational steering angle $\psi$ is also included, $$\Delta\tau_r = \frac{\sqrt{\left(y_r - \frac{c_0 t}{2}\sin\psi\right)^2 + \left(\frac{c_0 t}{2}\cos\psi\right)^2} - \frac{c_0 t}{2}}{c_0}$$

This may be approximated with a second order binomial expansion as:

$$\Delta\tau_r = \frac{y_r \sin\psi}{c_0} + \frac{y_r^2 \cos^2\psi}{c_0^2 t}$$

The first term represents steering and the second represents focusing.

The 90-degree phase shift operation can be accomplished in software by taking the complex conjugate of the Hilbert transform and beating the result against a complex carrier exponential $\exp(j\omega t)$ then taking the real part.

By transmitting waveforms on columns, and receiving signals on these columns as indicated, this dynamic receive elevation focusing approach may be combined with other existing pulse-sequences used with linear or phased arrays, such as scanline imaging, sector imaging, plane-wave compounding, diverging wave imaging or synthetic aperture imaging for transmit-receive azimuthal/lateral focusing. Unlike linear arrays, the present approach offers dynamic elevation focusing and additionally offers scan-plane steering for 3D imaging.

In one example, for a cardiac imaging probe, the desired elevational focus is between 4 to 10 cm in depth and the array is 12 mm in height. The pathlength difference between the edge of the array and the center of the array, each relative to the focal point for a 4 cm focus is sqrt(6^2+40^2)−40=0.4475 mm, which is smaller than an acoustic wavelength of 0.6 mm at 2.5 MHz. When focusing to a depth of 10 cm, the pathlength difference is only 0.1798 mm. Because these pathlength shifts are less than the acoustic wavelength, elevational focusing can be done on transmit and receive without need for phase-wrapping (and no need for compounding), and some limited elevational steering should be possible, enabling 2D image plane steering or 3D imaging. This approach may also enable tissue harmonic or contrast harmonic imaging. This scanline imaging (or plane-wave-compounding etc.) may be implemented with transmit sequences on columns, while using row biasing to create an elevational transmit focus. Then row bias voltages may be adjusted dynamically to achieve dynamic receive elevational focusing.

Figure 6:
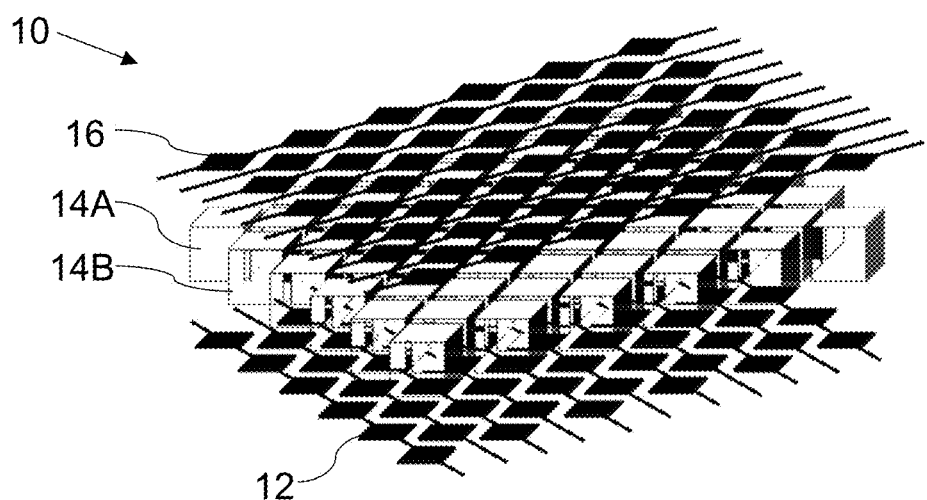
FIG. 6 is an illustration of an example of a SPARC array.

Diagonal Dicing Array Implementation: One way of making the array is to form an electrostrictive 1-3 composite, where the dicing of the composite is done at 45-degree angles relative to the row- and column electrode patterns, as shown in FIG. 6. Each square 14A, 14B represents a sub-element and may be comprised of a pillar in a 1-3 electrostrictive composite or a multiplicity of pillars in such a composite. Each square could also be comprised of a bias-sensitive CMUT element. The electrode patterns 12 and 16 may be such that active elements have ample electrode coverage in both first and second electrodes, but such that adjacent row electrodes address sets of elements aligned with alternating column subsets. As shown, adjacent rows and columns of electrodes 12 and 16 and sub elements 14A/14B may be offset.

Quadrant SPARC Arrays for Fast Readout: A SPARC Array can be fabricated such that columns and rows only span half the distance of the array in each direction but have a break in conductivity in the middle so as to make a quadrant-addressable array. A normal TOBE array would only require addressing from two sides of the array. A SPARC array requires addressing on all 4 sides. For a SPARC Array with N rows (N/2 row-pairs) and N columns (N/2 column pairs), this array would require 4N (rather than 2N for a traditional TOBE array) channels, but would enable aperture bias-encoded readout at 4 times the speed (factor of 2 due to columns divided into two halves and another factor of 2 owing to alternating elements, thus skipping of elements along a given row-pair).

Thus, while an 8-TX HEX-PD imaging sequence would require 8 transmits per orientation with a conventional TOBE array, it could be accomplished in only two transmits per orientation with a SPARC array. Alternatively, the 8 transmits could be put to use to read out on 32 binned columns or rows for improved HEX-PD imaging.

If uFORCES can be done with 8 transmit events using a TOBE array, it could be done with only two using uFORCES. This reduction in readout times may be useful for imaging fast-moving targets such as blood in carotid stenoses or heart valves.

Virtually Focused uFORCES: uFORCES (ultra-Fast Orthogonal Row-Column Electronic Scanning) suffers from poor SNR owing to effective transmission from only a single column element (or row element) at a time. Columns may be binned to enhance SNR but at the expense of resolution and image quality. By applying a synthetic phase to each column in a binned group of columns, a virtual focus may be achieved that is associated with each binned group.

The focal delay of element n at position $x_n$ for a focal depth F and steering angle $\theta$ may be given as $$\tau_n = \frac{x_n^2 \cos^2\theta}{2Fc}$$

Up to a second order paraxial/binomial approximation (and ignoring the tilt). The focal distance achieved without phase wrapping in a binned group of M elements of lambda pitch can be found by solving for F when $\omega_0 \tau_n = 2\pi$, and setting $x_n = M\lambda/2$. With no steering ($\theta = 0$), this becomes:

$$F = \frac{(M\lambda/2)^2}{2\lambda} = \frac{M^2\lambda}{8}$$

Thus, for a 5 MHz array with 16 binned elements to implement an 8-Tx uFORCES sequence with a 128×128 array (of 38.4 mm in size), a virtual focal distance of F=9.6 mm may be achieved without phase wrapping. This virtual focus could be in front of or in the back of the array and would achieve a reasonable effective f-number of $$f_\# = \frac{F}{D} = \frac{M^2\lambda}{8}\frac{1}{\lambda M} = \frac{M}{8}$$

for a lambda-pitch array. In the present case with M=16, $f_\#=2$. It may allow energy from every element of the array to be used in transmission with minimal image quality degradation.

Figures 7A, 7B:
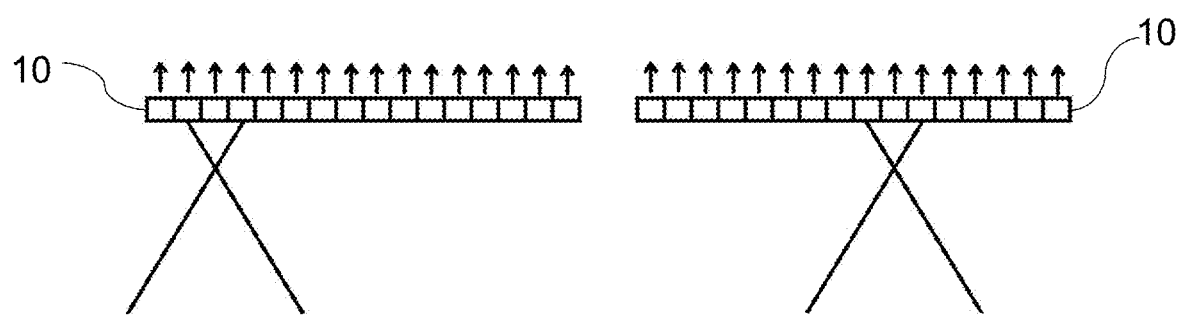
FIGS. 7A and 7B are illustrations of an example potential synthetic aperture imaging scheme using focal locations as virtual point sources.

Referring to FIG. 7, there is shown an illustration of a potential synthetic aperture imaging scheme using focal locations as virtual point sources. This may be implemented with a SPARC array 10 using phase-focusing. In implementing this scheme, columns (or rows) will be binned into G=8 groupings with M=16 elements per grouping. The desired complex weighting on each column will be $W_c = B_g e^{j\phi_m}$ where $c=g(M-1)+m$ and where $g=1, 2, \ldots, G$ is the grouping index, $m=1, 2, \ldots, M$ is the column index within a grouping and $c=1, 2, \ldots, GM$ is the column index over the array having N=GM columns. The amplitude weighting $B_g$ may take positive or negative values and will be sampled from a Hadamard matrix (or other invertible matrix), and this Hadamard pattern will change between transmit events. After aperture decoding with an inverse Hadamard matrix, it will be equivalent to transmitting with one binned grouping and receiving on all columns, then transmitting on the next binned grouping and receiving on all columns, etc., which may be followed by an image reconstruction algorithm. It will be appreciated that each binned grouping may achieve a virtual focusing effect. Let $b_g = |B_g|$ and $\varphi_m = \text{sign}(B_g)\phi_m$. In the case where $B_g$ is negative, the effective phase $\varphi_m$ is inverted relative to the desired phase $\phi_m$ needed for focusing. Thus, the sub-element bias voltages $[V_{g1}, V_{g2}]$ for the cosine and sine components of column c may be chosen such that $b_g = |B_g| = \sqrt{V_{g1}^2 + V_{g2}^2}$ and $\varphi_m = \arctan(V_{g2}/V_{g1})$. This approach may also be achieved using a conventional bias-sensitive TOBE array and using two transmit events rather than one to synthesize the desired complex aperture encoding.

The signal-to-noise ratio (SNR) gain of this approach is expected to be $M\sqrt{G}$ for a G-Tx-event sequence compared with transmitting on only one column at a time. For an 8-Tx uFORCES sequence with a bin-size of M=16 for a 128×128 array (or sub-array) this should be a gain of 45, which is even greater than the gain of FORCES ($\sqrt{128}=11$). A higher transmit voltage, coded excitation, or further coherent or incoherent averaging may be used over multiple transmit-receive events to further boost the signal-to-noise ratio.

Reconfigurable Elevational Lens: In the derivations above, it was predicted that and f-number of $$f_\# = \frac{F}{D} = \frac{M^2\lambda}{8}\frac{1}{\lambda M} = \frac{M}{8}$$

could be achieved without phase wrapping where M is the number of elements across an aperture for focusing, assuming lambda pitch. For a 5 MHz array, and M=32, $f_\#=4$, which is a commonly used f-number for elevationally-focusing acoustic lenses. This would achieve a focal depth of $$F = \frac{M^2\lambda}{8} = 3.84 \text{cm},$$

which is a reasonable focal depth for this transducer. Thus, synthetic phase methods could be used for out-of-plane focusing while any number of methods for in-plane imaging may be used, including walking aperture scanline imaging, sector-scan imaging, synthetic aperture imaging, plane-wave imaging, diverging wave imaging, etc. Moreover, the elevationally-focusing lens could be walked or steered across the elevation direction of the SPARC array for 3D imaging. This would be similar to a mechanically swept array but faster imaging may be achieved. For a 2.5 MHz probe, F=7.7 cm, which is reasonable for applications like cardiac imaging. A MATRIX probe could achieve something similar, given a limited acoustic window but the present approach can achieve wearable form factors and ultrafast B-scan rates (important for angle-independent flow imaging) which MATRIX probes cannot.

Improved SAFE Compounding: With SPARC arrays, it may be possible to improve on recently developed Simultaneous Azimuthal and Frensel Elevational (SAFE) compounding methods, which used bias-voltage encodable Fresnel lens patterns for elevation focusing while doing plane-wave or diverging wave compounding in the other dimension. Rather than using binary or tristate biasing to approximate the Fresnel lens, an arbitrary phase may be achieved to generate an improved Fresnel lens with fewer elevational focusing artifacts. An electrostrictive TOBE array and arbitrary-bias-voltage electronics requiring 4 transmits may be used to implement a single Fresnel elevational focus. This is because the total response is $h_{Tx/Rx}=h_{Tx}*h_{Rx}$ where $h_{Tx}$ and $h_{Rx}$ are the transmit- and receive-spatio-temporal impulse response functions, respectively, where $h_{Tx}=h_{Rx}=h$ when the transmit- and receive apertures are the same. Each h is implemented with a separate cosine- and sine-driving waveform: $h=h_c+h_s$. Thus, $h_{Tx/Rx}=(h_c+h_s)*(h_c+h_s)=h_c*h_c+h_c*h_s+h_s*h_c+h_s*h_s$. This thus requires 4 transmits to achieve each of the conditions of transmitting with a cosine-carrier and receiving with the weightings associated with a cosine carrier (c-c), then transmitting with a sine carrier and receiving with cosine weightings (s-c), then (c-s) then (s-s).

In contrast, the present SPARC array may involve only a single transmit event to implement a continuous-phase (rather than binary) Fresnel elevational focus. Other approaches may require 32 transmit events per B-scan slice, 4 per Fresnel Elevational focus, and compounding over 8 such Fresnel elevational focal depths to improve axial resolution, while using different diverging waves in the orthogonal direction. In contrast, with the present approach, imaging may be achieved using 4-times fewer transmit events to achieve essentially the same result. Thus, it may be possible to achieve B-scan imaging with only 8 transmit events. This may provide similar imaging speed compared to uFORCES and may offer improved SNR (owing to use of the whole aperture on transmit and receive rather than a sparse aperture), and may offer improved elevational focusing. This may then open up opportunities for real-time volumetric imaging with appreciable motion.

Tissue Harmonic Imaging: The present method may be amenable to tissue harmonic imaging as it can create focused beams that will undergo nonlinear propagation. This is important for cardiac imaging. If the transmit frequency is 2.5 MHz, the receive frequency will be 5 MHz, and dynamic receive focusing may be able to be implemented from deep in tissue to as close as $$F = \frac{M^2\lambda}{8} = 3.84 \text{cm}$$

for M=32 (300 micron-pitch elevational elements), without phase wrapping.

Switching Bias Patterns Between Transmit and Receive: There may be a number of schemes where it may be advantageous to switch bias patterns after a transmit event and before receiving signals, where the switching time is an effective dead zone, or ramping bias voltages could even be used as an effective time-gain compensation. For example, in uFORCES, elevation focusing is accomplished only with transmit focusing. But if one switches off column biases and instead turns on row biases to achieve a dynamic synthetic parabolic phase, one can achieve an effective form of dynamic receive focusing in elevation. This may be limited to weak f-numbers but may be advantageous in some situations. In some examples, a parabolic phase or delay may be applied across columns of elements to implement azimuthal focusing, and/or a parabolic phase or Frensel Lens may be applied across rows of elements to implement elevational focusing.

Programmable Bias Voltage Implementation: One challenge of achieving programmable phase for each element in a column is the requirement for row bias voltages to be programmable, arbitrary-level and ideally time-varying during a receive event to implement dynamic receive focusing.

An arbitrary-level bias voltage with high voltage DACs and current source voltage follower may be implemented with AD5535 or HVDAC200.

Figure 8:
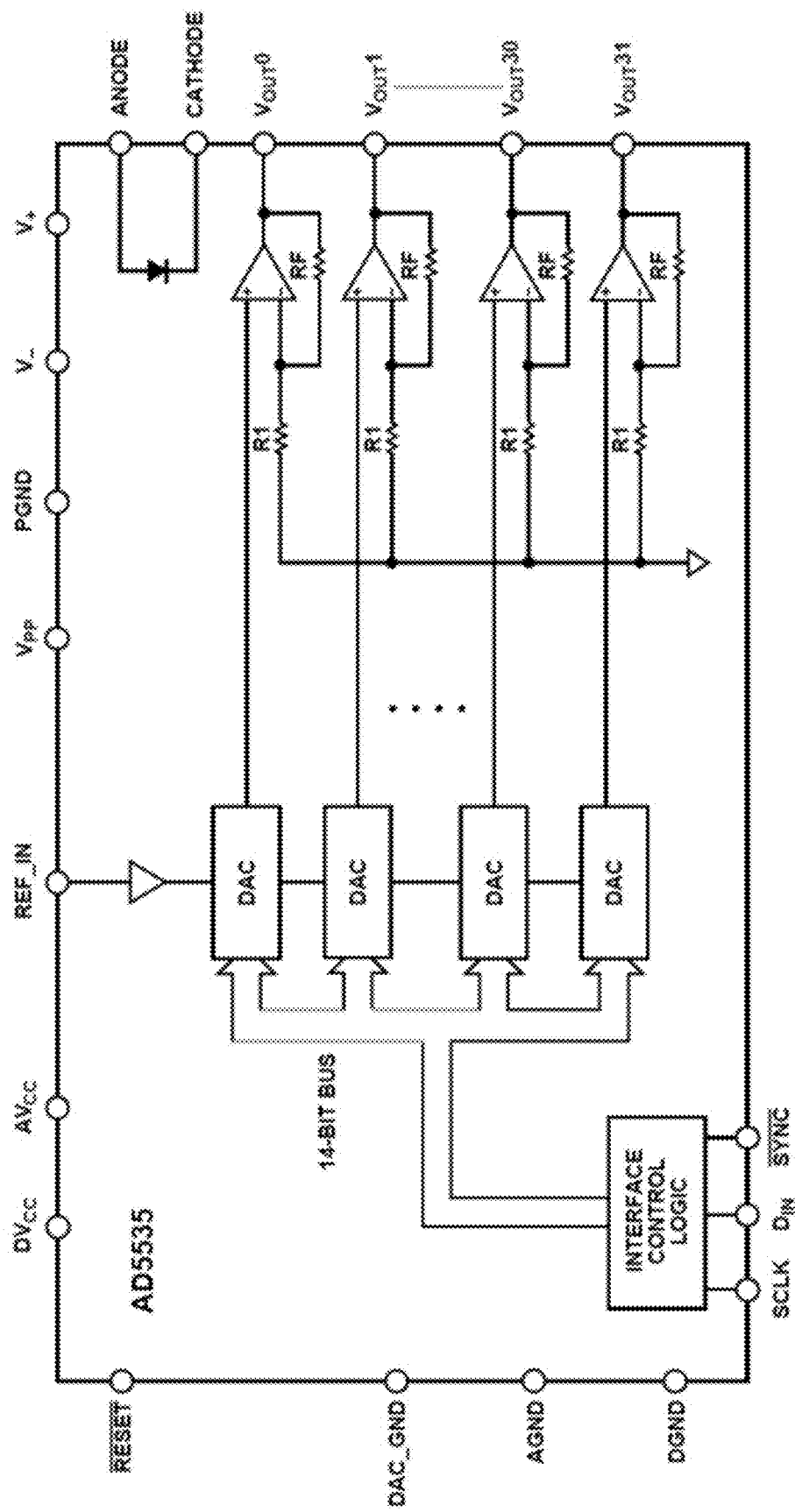
FIG. 8 is a block diagram of an arbitrary level bias voltage generator.

The AD5535 is a 32-channel, 14-bit DAC with an on-chip high voltage output amplifier. The output voltage range is programmable via the REF_IN pin. The output range is 0 V to 50 V when REF_IN=1 V, and 0 V to 200 V when REF_IN=4 V. Each amplifier can source 700 µA. The selected DAC register is written to via a 3-wire interface. The serial interface operates at clock rates of up to 30 MHz and is compatible with DSP and microcontroller interface standards. It can drive a 200 pF capacitive load, which is probably not enough to directly drive the present TOBE array elements. Thus, the output of this circuit could be used as an input to a current source voltage follower, e.g., using a PFET and NFET pairs and capacitor banks (such capacitor banks can be common to all channels), to supply the desired voltages with sufficient transient currents. Referring to FIG. 8, an example of a circuit for arbitrary level bias voltage generation is shown.

A new pattern of voltages may be written in (32*14)/30e6=15 us. For a 7.5 cm imaging depth, the round-trip distance is 150 mm. At 1.5 mm/us, this is a round-trip time of 100 us. Thus, bias-encoding may be used to change the receive focus about 6 times during a transmit-receive event. Another option is HV257, a 32-Channel High Voltage Sample and Hold Amplifier Array.

Figure 9:
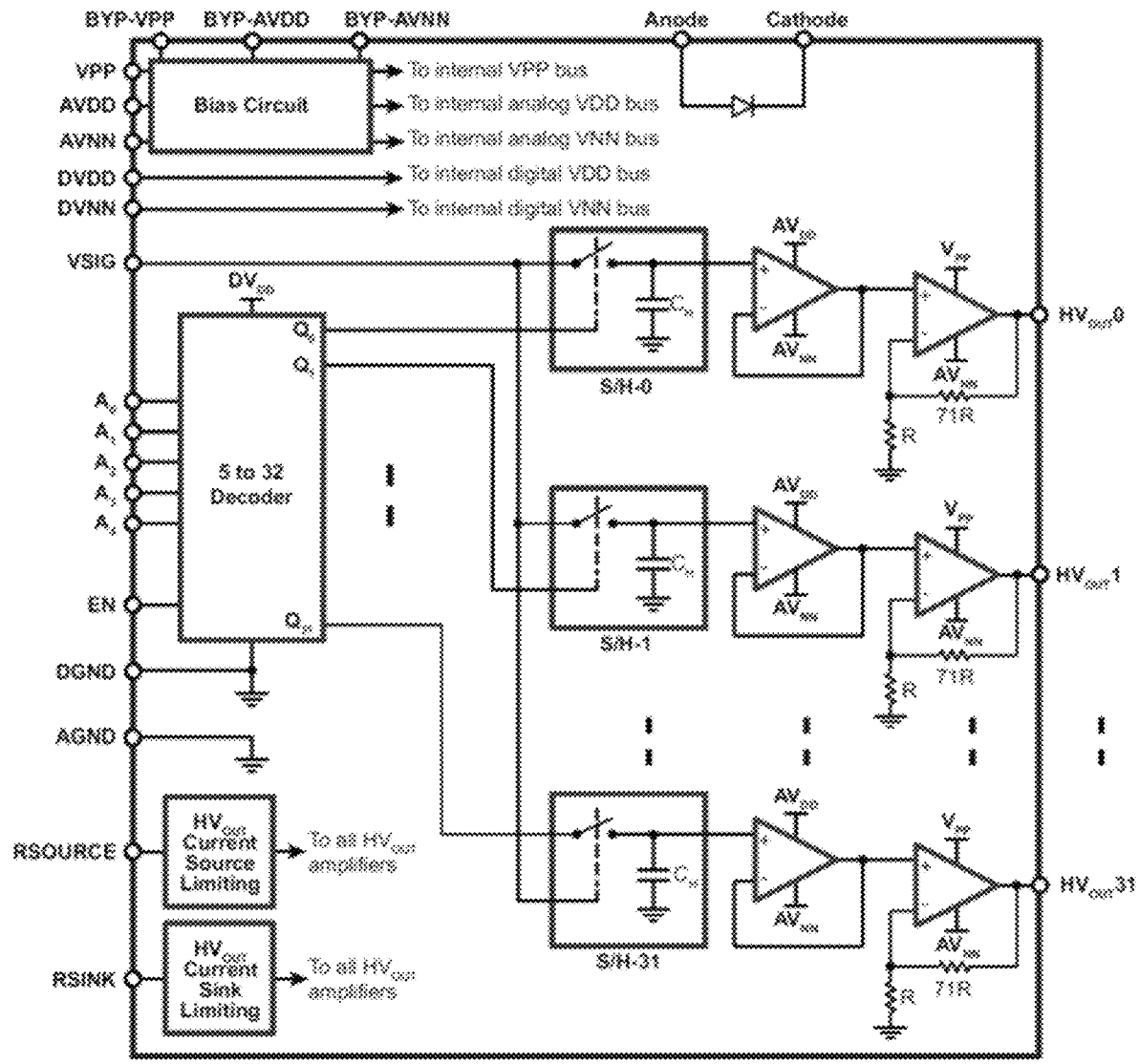
FIG. 9 is a block diagram of an alternate example of an arbitrary level bias voltage generator.

Arbitrary-Level Bias Voltages using Low-Voltage DACs and Power Op-Amps or MOSFETS (potentially with a Current Source Voltage Follower): A low voltage DAC (e.g., MAX5631, which is a 32-channel unit) may be used as a gate input to a Power Op-Amp to produce an tunable high-voltage output. The output, however, will be nonlinear and have un-even steps. For example, OPA541AP is a power-op-amp that can be used as programmable high-voltage source. Another option is HV257, a 32-Channel High Voltage Sample and Hold Amplifier Array. This takes a single analog input (up to 5V) and uses a 5 by 32 decoder to write high voltages to a sample and hold array. It can drive capacitive loads up to 3 nF. A single element of the present array, which is 200 microns by 20 mm, assuming a PMN composite dielectric constant of 4000 and a thickness of 180 microns would be 0.787 nF. A current source voltage follower circuit with large capacitor banks could also be used to ensure the desired voltages are supplied with needed current transients. It may have a 2.2V/us slew rate so one could go from 0 to 250V in 113 us, which may be fast enough for some but not all applications. It is also not clear if this would survive high voltage pulses from the ultrasound system. This example of arbitrary bias voltage electronics is shown in FIG. 9.

Other Methods: The above methods may be voltage limited to ~50V since high-voltage op-amps may be limited such voltages. This may be fine for high-frequency ultrasound applications (e.g., 10 MHz) but for lower diagnostic frequencies, the electrostrictive material needs to be thicker, resulting in the requirement for higher voltages to achieve the same biasing electric field. A 2.5 MHz electrostrictive transducer may need 200V biasing, and this may be difficult to achieve with the above methods.

One way to overcome these limitations may be to use or modify the high-voltage MOSFET based biasing electronics but turn on $V_{pp}$ or $V_{nn}$ for a fixed amount of time while the voltage ramps to a desired level, loading this voltage onto an additional capacitor prior to the bias tee, then switching to a high-impedance state to keep the charge loaded.

Figure 10:
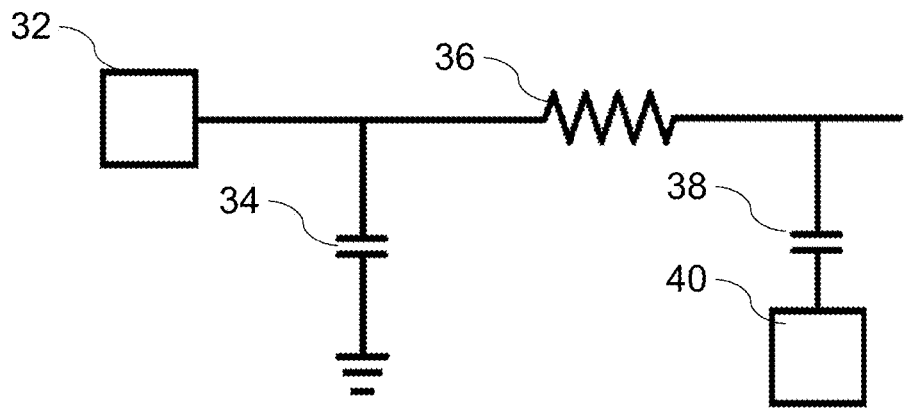
FIG. 10 is a block diagram of a further example of an arbitrary bias voltage electronics.

Referring to FIG. 10, another example of an arbitrary bias voltage generator. A Pi-Card 32 uses MOSFET switching to switch between +HV, −HV, ground, and a high-impedance state. A capacitor 34 may be provided to help hold the bias voltage in parallel with a bias tee on an interface board, which includes a resistor 36 and capacitor 38 that is connected to an ultrasound system 40, such as a Verasonics™ system. The time which +HV or −HV is on is used to ramp a voltage, loaded on the extra capacitor. The voltage can be switched to a high impedance state when the desired voltage is reached. The Verasonics™ system 40 is a programmable ultrasound platform, but any ultrasound system with pulsing and receiving capabilities could be used here.

The Pi-cards 32 includes high-voltage bias switching electronics, one embodiment of which is described below. The voltage loaded on the additional capacitor will be controlled by the bit sequence controlling how long Vpp or Vnn are on for, as well as by the ramping time (which may be load dependent).

Figure 11:
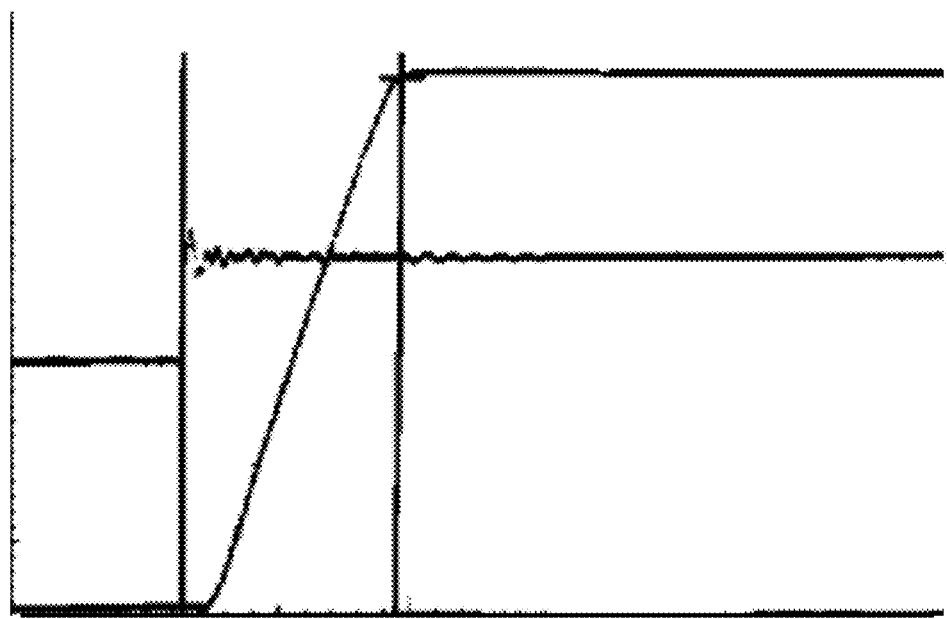
FIG. 11 is a graph depicting voltage ramping time.
Figure 12:
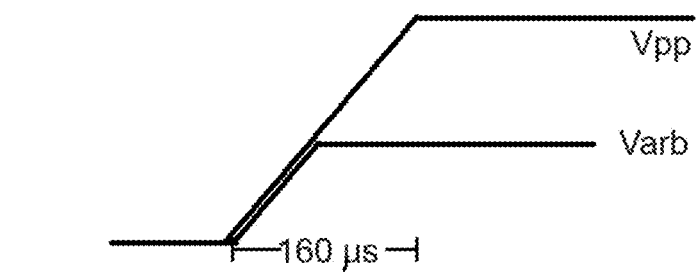
FIG. 12 is a graph of a bit-sequence as a function of time to load an arbitrary voltage $V_{arb}$ onto a storage capacitor.

Referring to FIG. 11, a graph of a voltage ramping time is shown, and in FIG. 12 a graph of the bit-sequence as a function of time to load an arbitrary voltage $V_{arb}$ onto the storage capacitor is shown.

Figure 13:
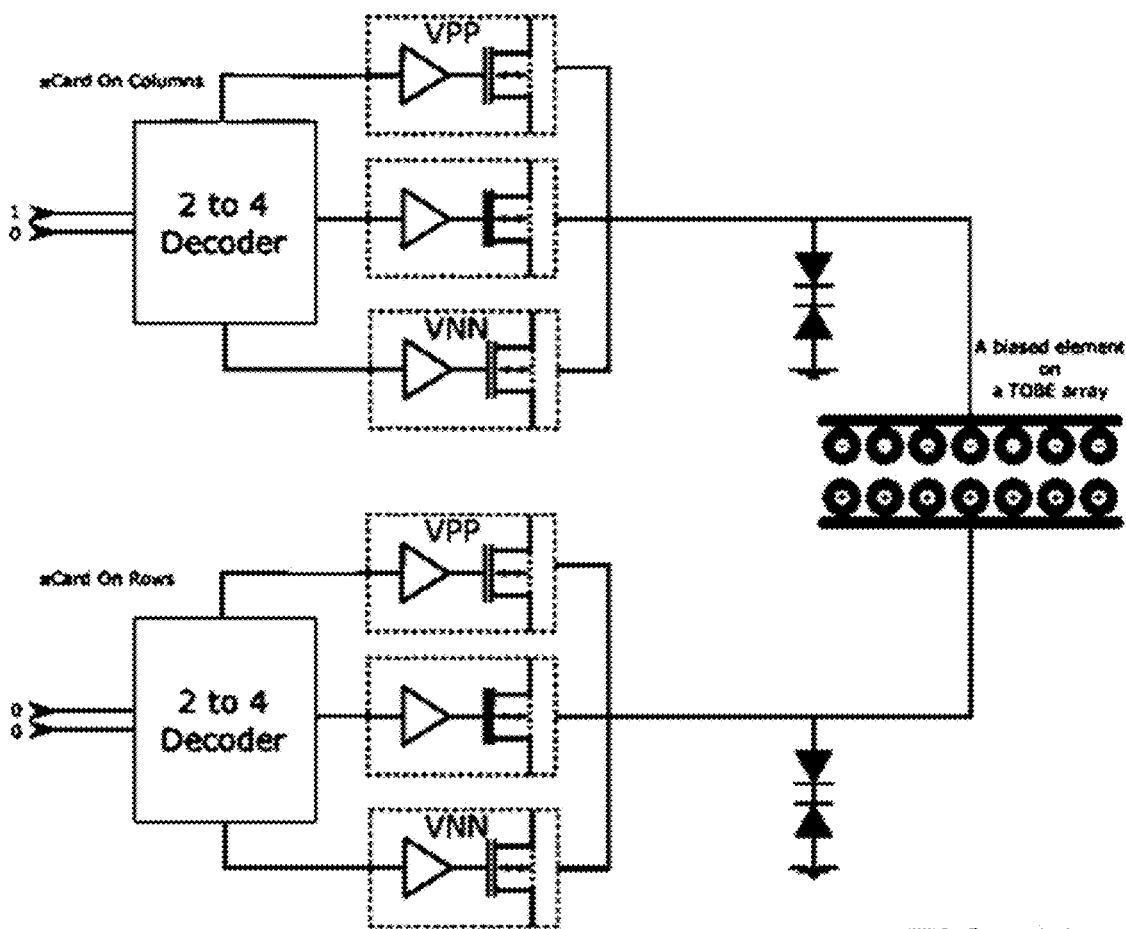
FIG. 13 is a block diagram of a high-voltage bias switching circuit.
Figure 14:
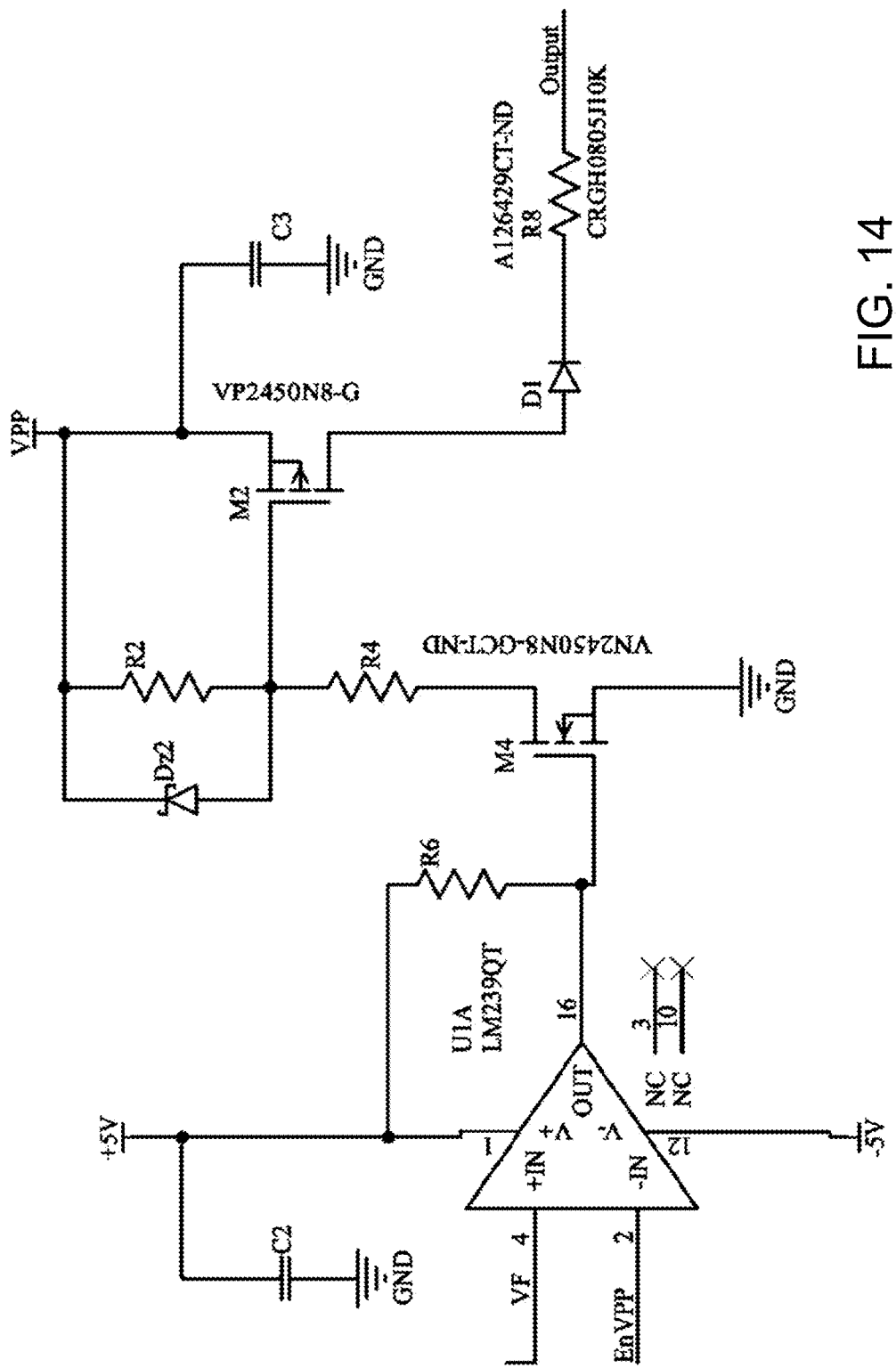
FIG. 14 is a diagram of a high voltage switching circuit for $V_{pp}$.
Figure 15:
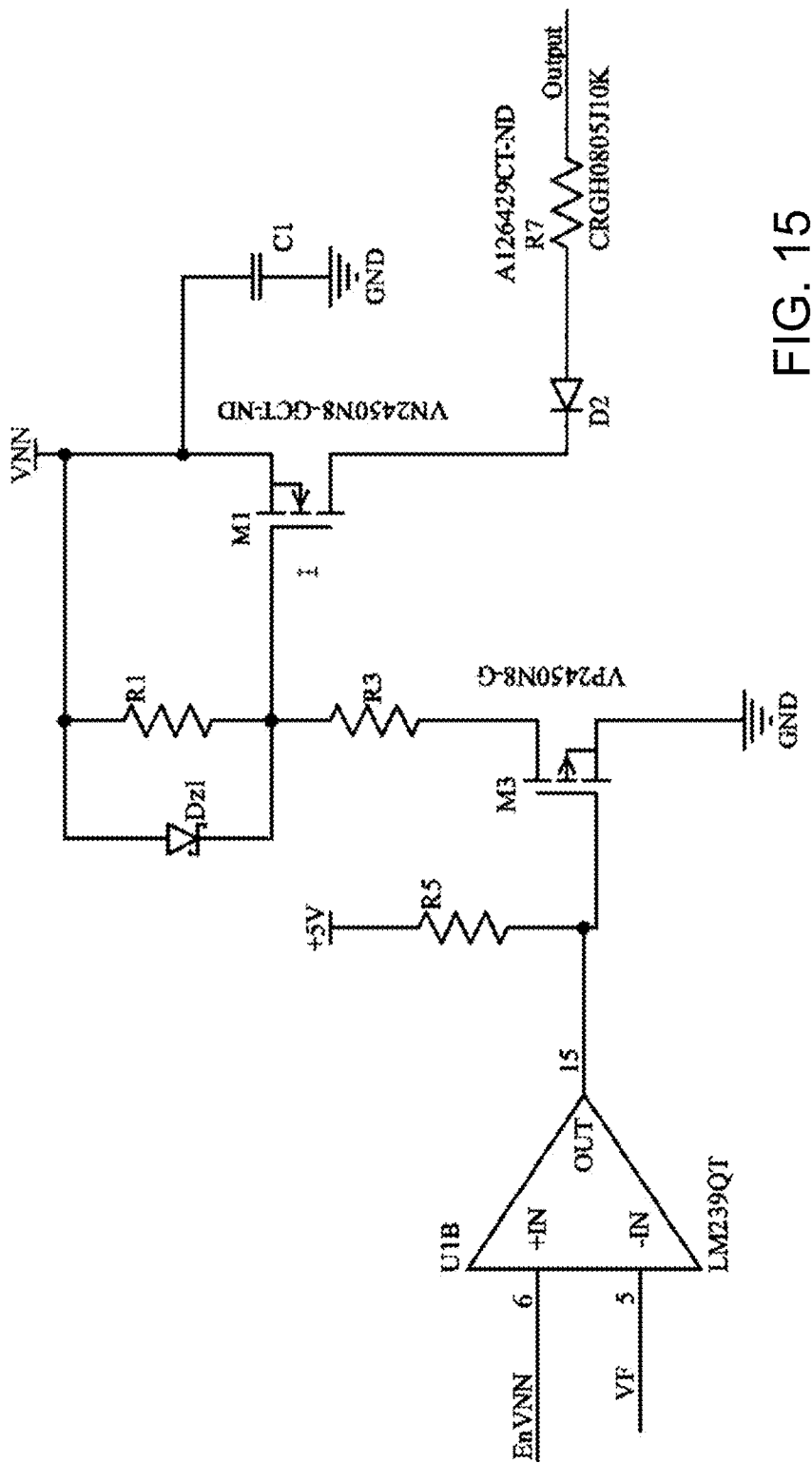
FIG. 15 is a diagram of a high voltage switching circuit for $V_{nn}$.
Figure 16:
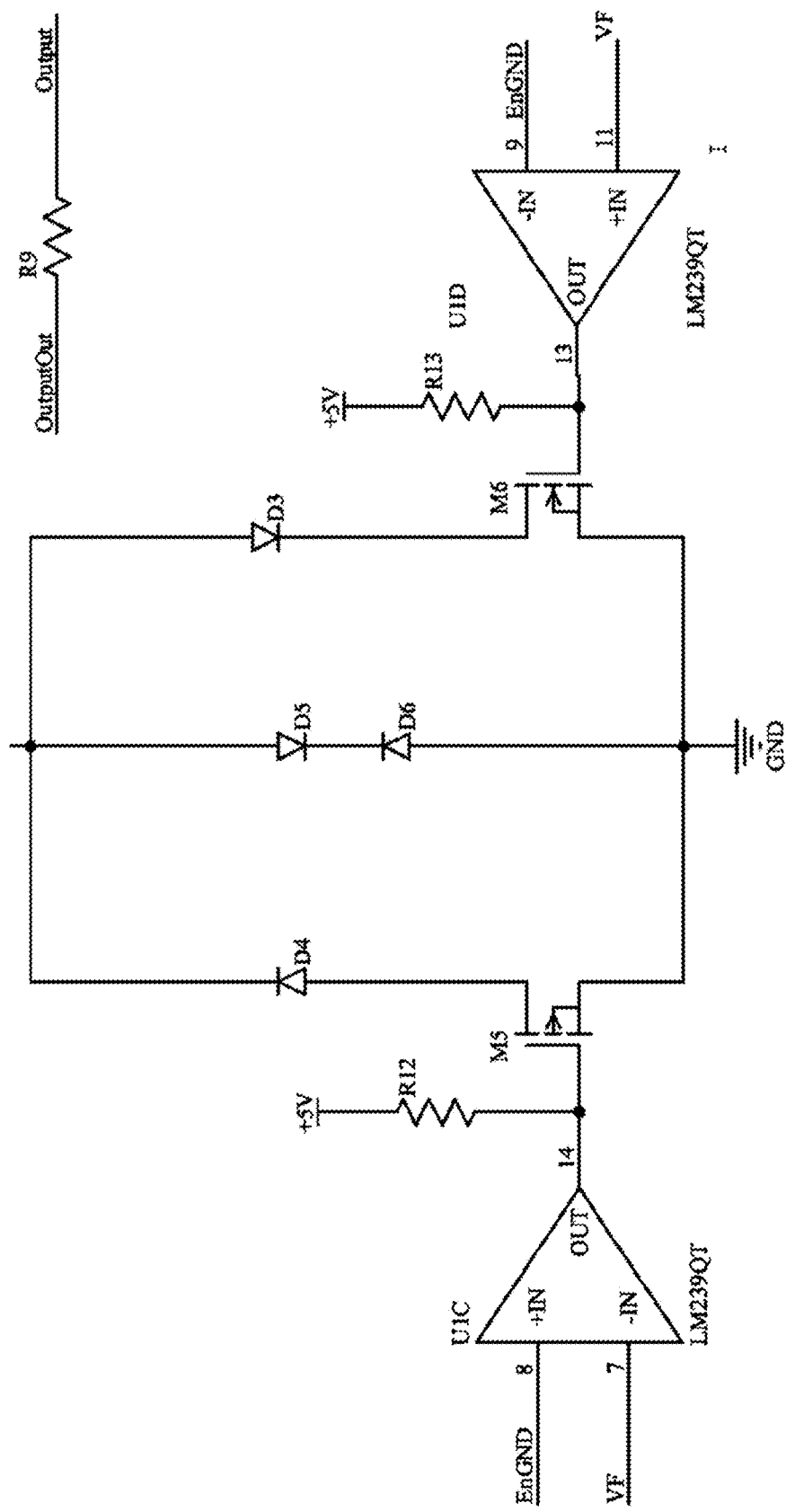
FIG. 16 is a diagram of a high voltage switching circuit for actively driving the bias voltage to Ground.

A further for the fast bias switching electronics is shown in the schematic depicted in FIG. 13. An example of high-voltage switching electronics for $V_{pp}$ is shown in FIG. 14 and an example of high-voltage switching electronics for $V_{nn}$ is shown in FIG. 15. An example of high voltage switching electronics for actively driving the bias voltage to Ground is shown in FIG. 16.

Figure 17:
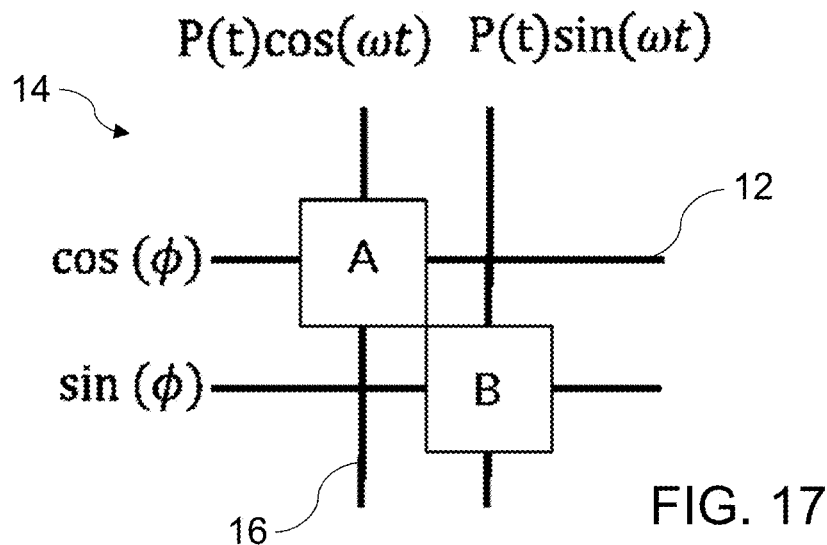
FIG. 17 is a detailed view of a transducer element and sub-elements.
Figure 18:
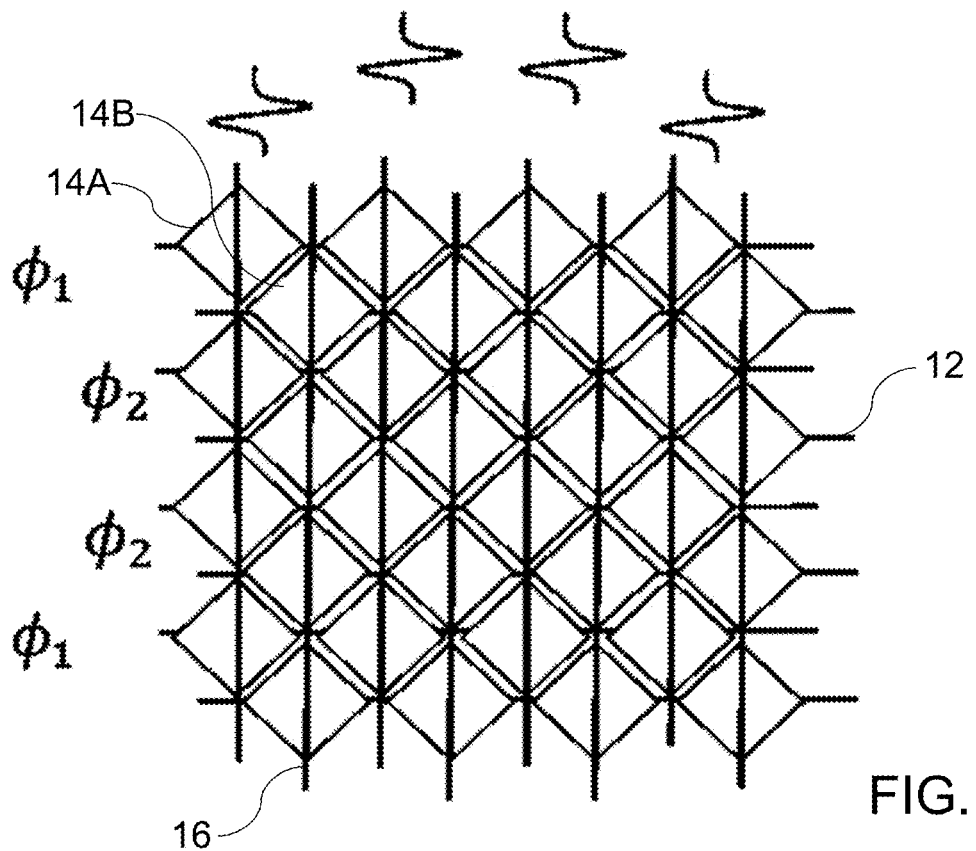
FIG. 18 is a diagram of a condensed SPARC array with diamond shaped elements.

An Array System or Imaging System: The array described herein, which may include an alternating row-column array and arbitrary level biasing electronics as shown in FIGS. 17 and 18, may be a standalone array sub-system that connects to an ultrasound system with transmitting and receiving electronics, or the desired programmable biasing electronics may be incorporated into a system with transmitting and receiving electronics. In some examples, the electronics may include biasing electronics with programmable levels, high-voltage transistors, digital to analog converters, programmable variable resistors, DC-to-DC converters, pulse-wave modulation electronics, or combinations of these elements, and the controller may include a GPU, a CPU, an FPGA, an ASIC, and/or multiples or combinations of these elements. The various aspect or elements of control may be combined or integrated into one block or separated between different components whether between transmit events, receive events, or both transmit and receive events as discussed above.

The system may take various forms, and may be incorporated into a housing with a form factor that is planar, concave, convex, plano-concave, plano-convex, biconcave, or other suitable shape. The system may be implemented has a handheld or wearable device, and may be deployed in trans-esophageal, transrectal, transvaginal, endoscopic or laparoscopic applications.

Simulations: For the SPARC arrays, the elements work in pairs to create a phase difference that can be used to steer a beam. As can be seen in FIG. 17, each element pair is made up of an A element driven by a cos wave and given a bias voltage of $\cos(\phi)$ and a B element driven by a sin wave and given a bias voltage of $\sin(\phi)$. With the use of some trig identities, it may be found that the combined signal has a phase difference of −φ. This phase difference can then be used to steer an ultrasound beam. Phase steering works by adjusting the phase of each row such that the pulses will arrive in phase at the desired focal point and so that constructive interference is achieved.

$$A = P(t)\cos(\phi)\cos(\omega t)$$

$$B = P(t)\sin(\phi)\sin(\omega t)$$

$$A + B = P(t)\cos(\phi)\cos(\omega t) + P(t)\sin(\phi)\sin(\omega t) = P(t)\cos(\omega t - \phi)$$

An arbitrary-level bias voltage with high voltage DACs and current source voltage follower may be implemented with AD5535 or HVDAC200. Referring to FIG. 17, the layout of a single element pair of transducers is shown as part of a transducer element 14. Bias voltages are applied on the second (or row) electrodes 12 and the signals are sent on the first (or column) electrodes 16. FIG. 18 shows the condensed SPARC array with diamond shaped elements and a representation of the phase and delay steering. The result is an array that can do azimuth steering using phase and elevation steering using delays independently from each other. This is represented in FIG. 18. Such an array may allow for the steering of an ultrasound beam anywhere in the 3D plane.

Simulation Design: For all simulations, Field II may be used and accessed it through MATLAB. Because of limitations to Field II's ultrasound simulation options for 2D arrays, some methods are far from conventional. For one, Field II does not allow for the creation of diamond shaped transducer elements so the transducer may be set up by first creating a regular 2D square array, removing the corners, and then rotating it 45 degrees. This process, which can be seen in FIG. 19A-19C, creates the desired array shape, and with it, a host challenges. The indexing of elements becomes complex, and because a 2D array cannot be rotated by 45 degrees in Field II, the x and y planes of the transducer are no longer aligned with the x and y planes being observe and worked with.

Referring to FIG. 19A, a rough representation of how the SPARC array was set up in Field II is depicted. To deal with this, the coordinates of each element were found, rotated 45 degrees, and then each diamond replaced with two triangles (Field II does have an option to create an array with triangular elements). However, this resulted in the appearance of strange unexplained artifacts in the pressure field plots. It also meant that there were double the elements which caused both an increase in the program run time and made the simulations more complex to work with. The process was stopped after the first step and the observation plane was rotated 45 degrees as shown in FIG. 19C. This also was far from a perfect solution and led to difficulties when trying to index the elements.

Figure 20A:
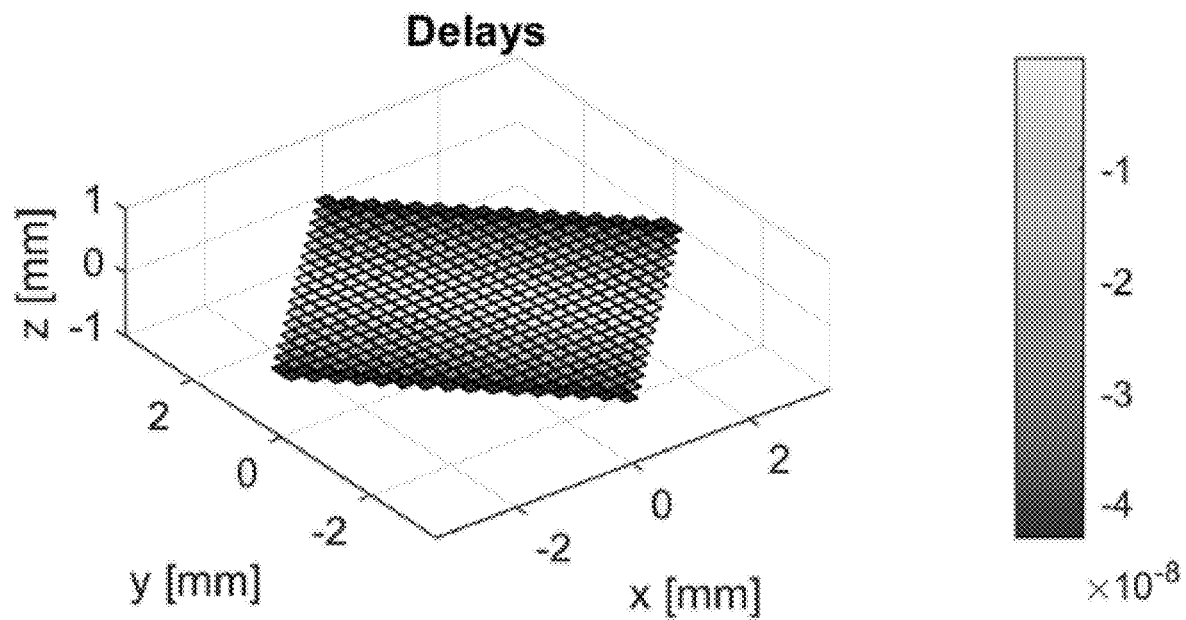
FIGS. 20A and 20B are graphs depicting the delays and apodization assigned to an example of a 16×16 element pair array with a pitch of $\lambda/2_{3/2}$ and a center frequency of 2.5 MHz focused at 40 mm away from the transducer.
Figure 20B:
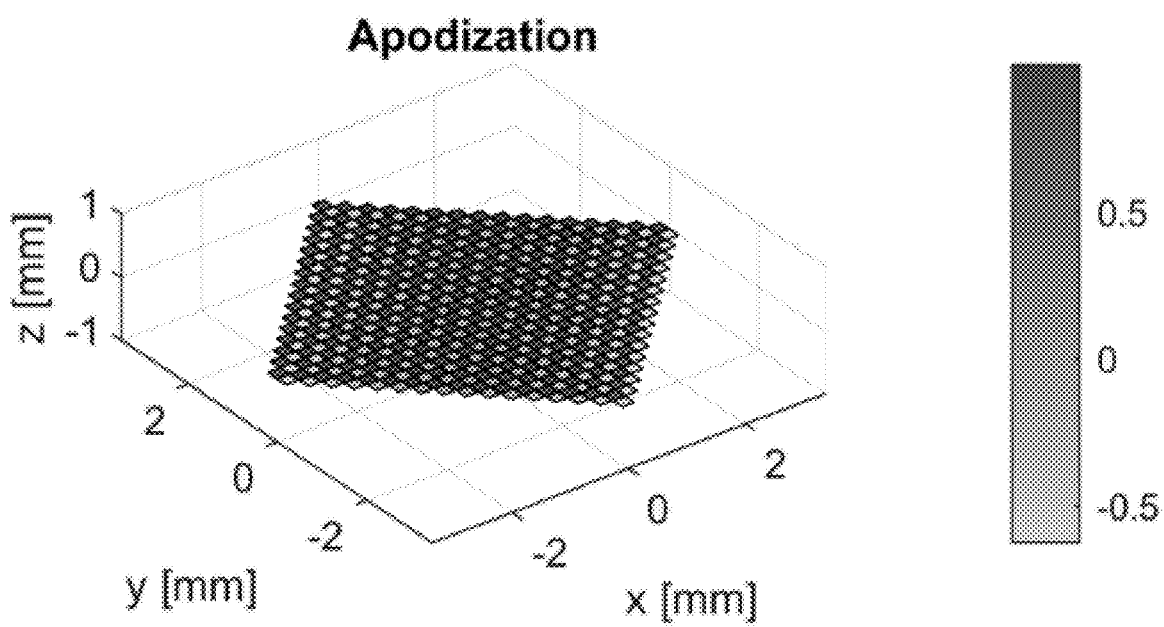

Referring to FIG. 20, the delays and apodization assigned to a 16×16 element pair array with a pitch of $\lambda/2^{3/2}$ and a center frequency of 2.5 MHz focused at 40 mm away from the transducer are depicted.

Figure 21A:
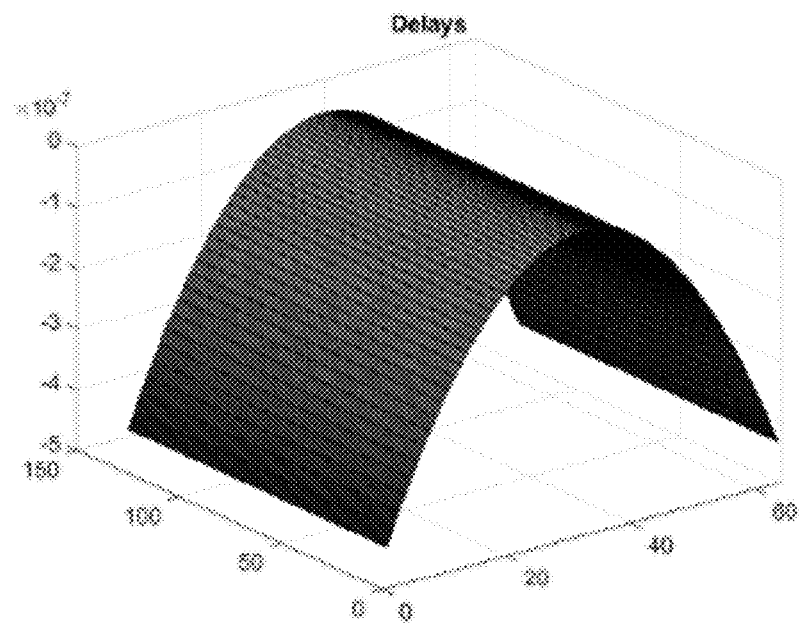
FIGS. 21A and 21B are graphs depicting the delay and apodization profile for a cardiac SPARC array.
Figure 21B:
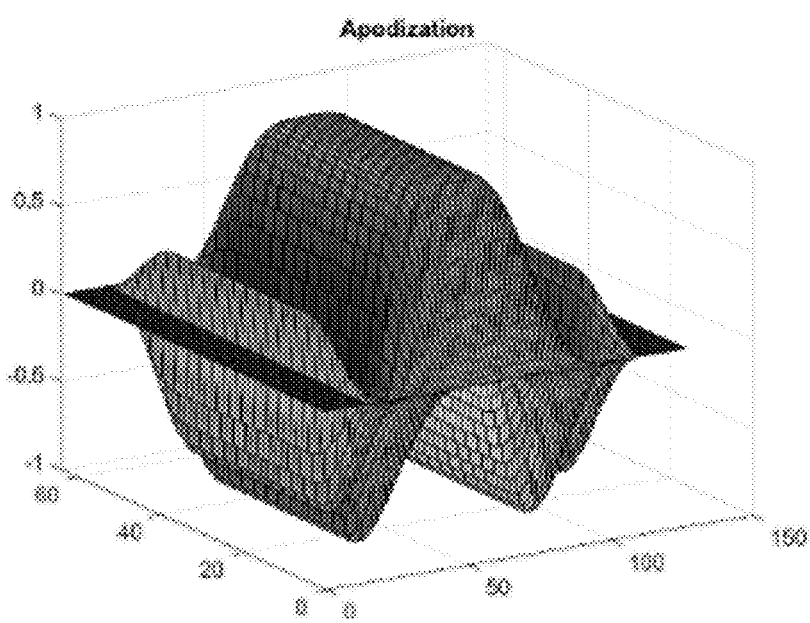

To simulate the SPARC arrays, the ele_apodization function was used to mimic the effects of the bias voltages and ele_delay was used to set the signal delays. An example transducer can be seen in FIG. 20. ele_waveform was used to set the alternating cos and sin waveforms. Referring to FIGS. 21A and 21B, the delay and apodization profile, respectively, for a cardiac SPARC array are depicted.

The simulations were in the context of a wearable cardiac probe with 64×48 element pairs (6,144 total elements and 224 total channels). The array has a centre frequency of 2.5 MHz and a pitch of $\lambda/2^{3/2}$. These parameters were chosen as they reflect the standard dimensions of cardiac probes in use today, and give the described dimensions of 20×14 mm. To simulate this array, a 64×64 element array was set up. Then for the first and last 8 row pairs, the apodization was set to zero, which gives the array its dimensions. A Hanning apodization was also applied to the whole array in order to improve axial resolution. The apodization and delay profile for this array when being steered directly forward and focused at a distance of 70 mm from the array are shown in FIG. 21.

Simulation Results

Pressure Field Functions: The resultant pressure fields were first from different transducers. This was done by using the calc_hp function to find the max pressure at every pixel in the desired image plane. The data was then normalized and displayed with a 40 dB dynamic range. This allowed the steering and focusing capabilities of each transducer to be visualized. The results from the more novel phase steering were compared to the more conventional method of delay steering. To do this the observation plane was rotated 90 degrees and the plane was considered on which the array would steer with just delays or just phase. This allowed relatively easy comparisons to conventional methods without having to change the transducer being used.

Figure 22A:
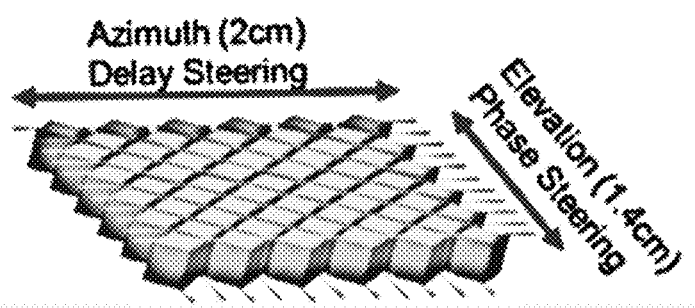
FIG. 22A depicts an example of a SPARC array.
Figures 22B, 22C:
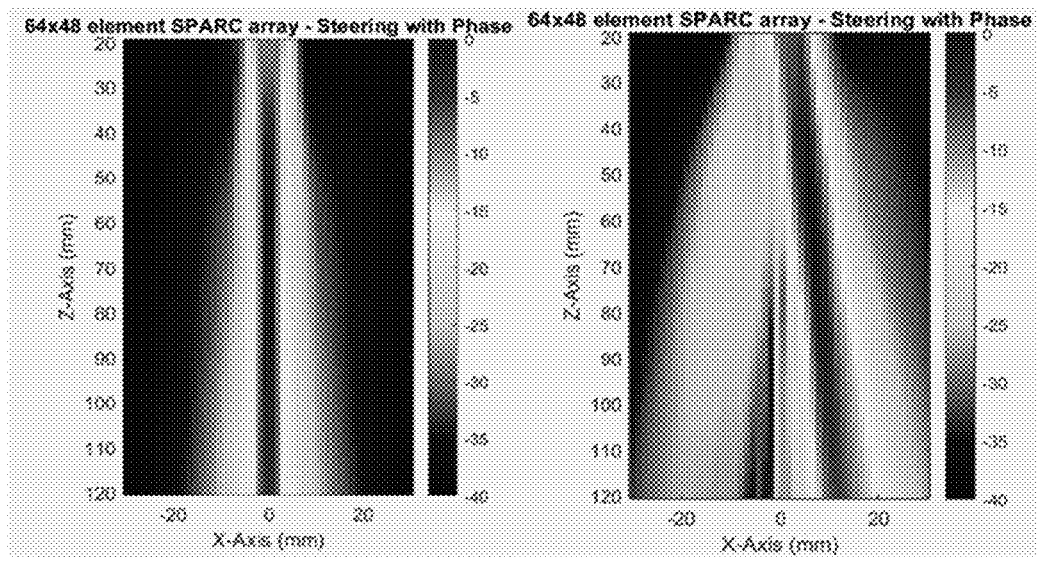
FIG. 22B is an image obtained from an example of a SPARC array with 64×48 element pairs having a focal point that is steered straight ahead using elevational steering.
FIG. 22C is an image obtained from an example of a SPARC array with 64×48 element pairs having a focal point that is steered 5 degrees off center using elevational steering.
Figures 22D, 22E:
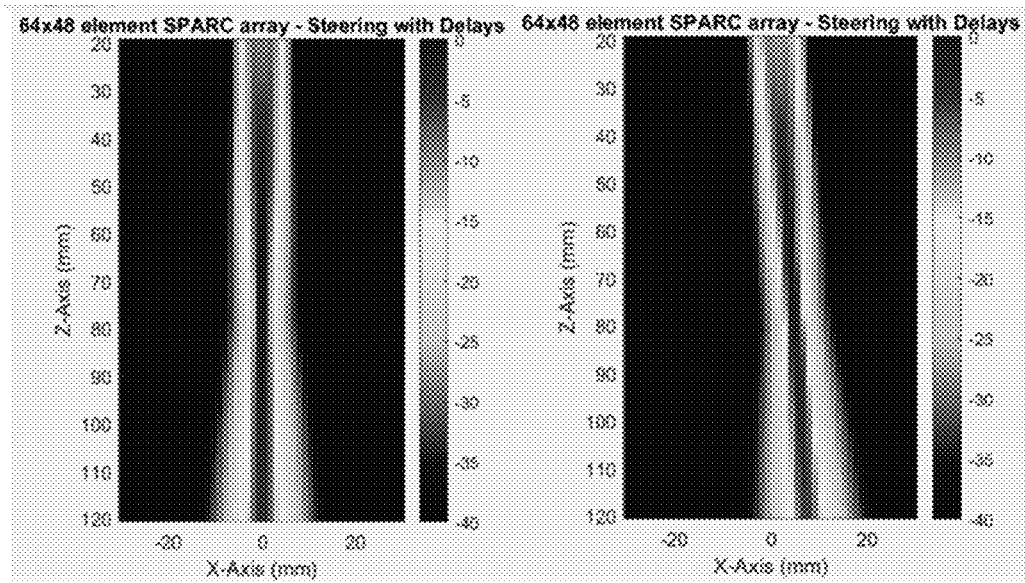
FIG. 22D is an image obtained from an example of a SPARC array with 64×48 element pairs having a focal point that is steered straight ahead using azimuthal focusing.
FIG. 22E is an image obtained from an example of a SPARC array with 64×48 element pairs having a focal point that is steered 5 degrees off center using azimuthal focusing.

As can be seen in FIG. 6, other than an increase in noise, phase steering had similar capabilities as delay steering. The array used is shown in FIG. 22A. The pressure fields from a SPARC array with 64×48 element pairs (6 144 elements total) are depicted in FIG. 22B-22E. The focal point is 70 mm away from the array, where FIGS. 22B and 22D are steered straight ahead and FIGS. 22C and 22E are steered 5 degrees off center. The arrays have a center frequency of 2.5 MHz and a pitch of $(\lambda/2)^{3/2}$. The array has dimensions of ~20×14 mm. Between FIGS. 22B and 22D, when steering straight forward, both phase steering and delay steering could produce an isolated beam with little extra noise. In FIGS. 22C and 22E, it can be seen that when steering away from center, the phase steering could still produce an isolated beam, however it comes with a significant amount of noise when compared to the more conventional delay steering. It should also be noted that, as the beam was steered further away from the center, the phase steering became worse, and more noise was produced.

These pressure field images demonstrate that SPARC arrays may allow for focusing an isolated beam on a selected point in three dimensions. Thus, giving it the capability of 3D imaging or, at the least, the ability to image on any desired plane.

Point Spread Functions and Cyst Phantoms: Once the possibility of phase plane imaging was confirmed, point spread functions (PSFs) were developed to explore its viability. To do this, a beam was steered across a plane and at each angle Field II's calc_scat was used to give the A-scan. The A-scans were compared to create a rectangular B-scan. After normalizing the data, the scanConversion® function was used to convert from a rectangular image to a sector image. The resultant image was then compared with a 40 dB dynamic range.

Figure 23A:
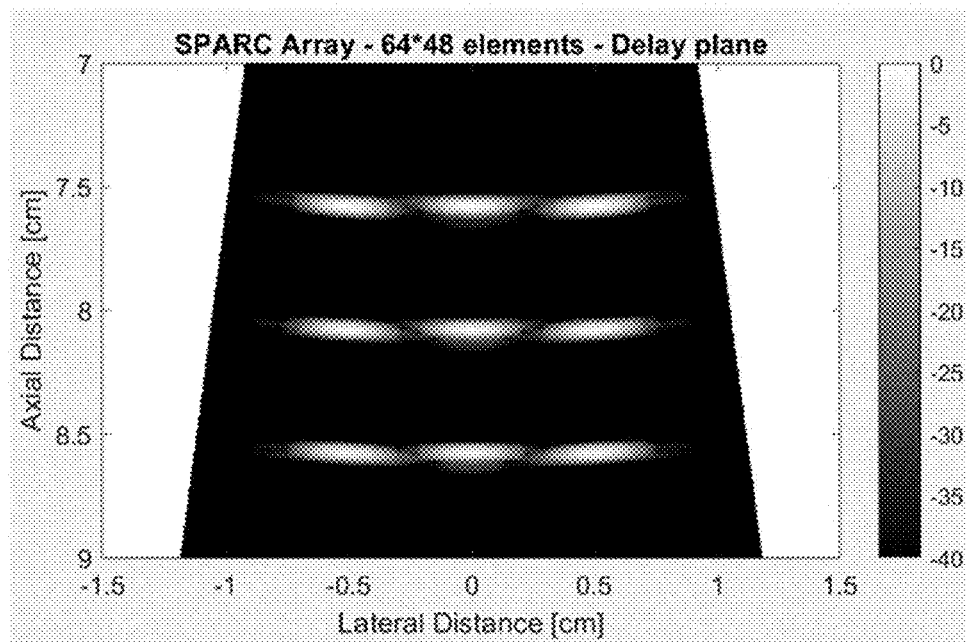
FIG. 23A is a cardiac image using a SPARC array showing the point spread function (PSF) obtained by steering using the delay only.
Figure 23B:
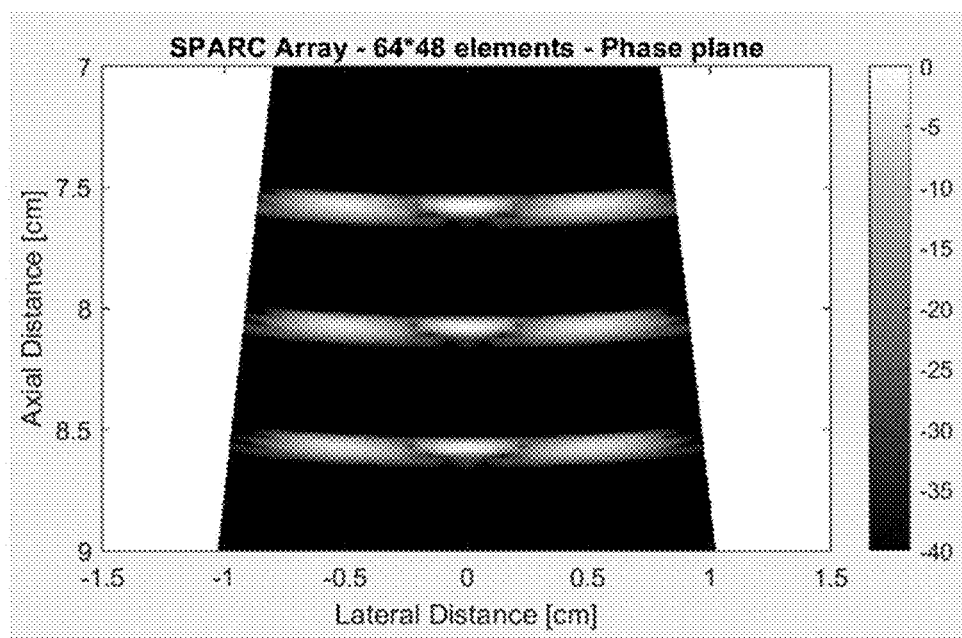
FIG. 23B is a cardiac image using a SPARC array showing the PSF obtained by steering using the phase only.

Referring to FIGS. 23A and 23B, imaging maps of PSFs with 9 points at 75, 80, and 85 mm all 5 mm apart, imaged with a cardiac SPARC array with a center frequency of 2.5 MHz, where FIG. 23A shows the PSF for only steering with delays and FIG. 23B shows the PSF for only steering with phase. As can be seen in FIGS. 23A and 23B, the results were similar to the pressure field plots. The phase plane imaging is still occurring and still viable. However, it has significantly more noise than the delay steering. This noise also becomes worse by steering further away from the center. To improve resolution, a dynamic receive beamforming may be arranged with a process where the focus is changed as a function of time such that signals are received in focus.

Figure 24:
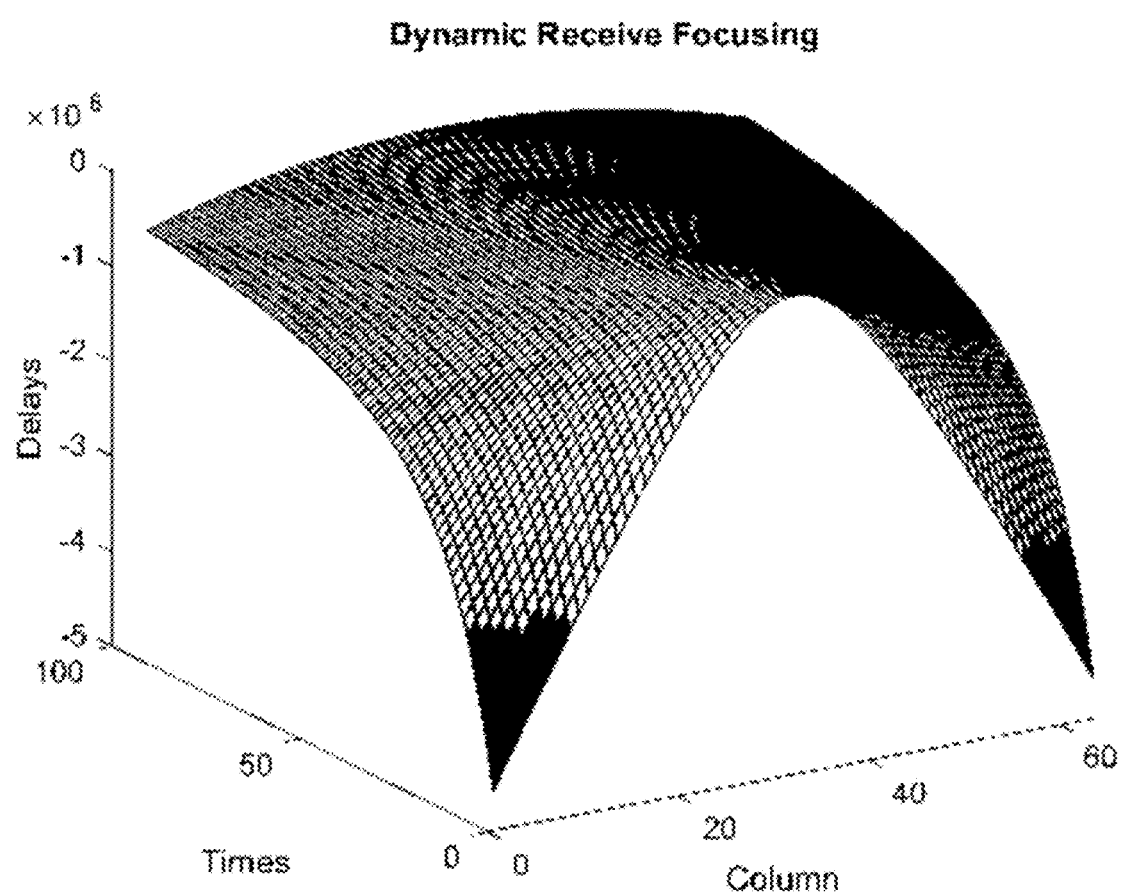
FIG. 24 is a representation of the focusing timeline for a 64×48 element cardiac SPARC array.

Referring to FIG. 24, a representation of the focusing timeline for a 64×48 element cardiac SPARC array is depicted. The representation was achieved by dynamic beamforming implemented in Field II using the function xdc_focus_times in the delay direction and xdc_apodization in the phase direction. Both functions allowed a focus timeline to be created and to set it such that the receive aperture would always receive signals in focus. The following equation may be used to determine the required delays:

$$\Delta \tau = \frac{-\left(\sqrt{(y - c_0 t \sin(\theta))^2 + (c_0 t \cos(\theta))^2} - c_0 t\right)}{c_0}$$

where $\Delta \tau$ is the delay of each column, y is the distance each element is from the center, t is the time taken for the signal to reach the transducer (note the one-way distance was used as that is what is used by Field II), c0 is the speed of sound in the medium, and $\theta$ is the angle of steering. To find the desired apodization for the rows, $\phi = 2\pi f0$ may be used, where f0 is the center frequency and then alternate between $\sin(\phi)$ and $\cos(\phi)$ on the rows.

Figures 25A, 25B, 25C:
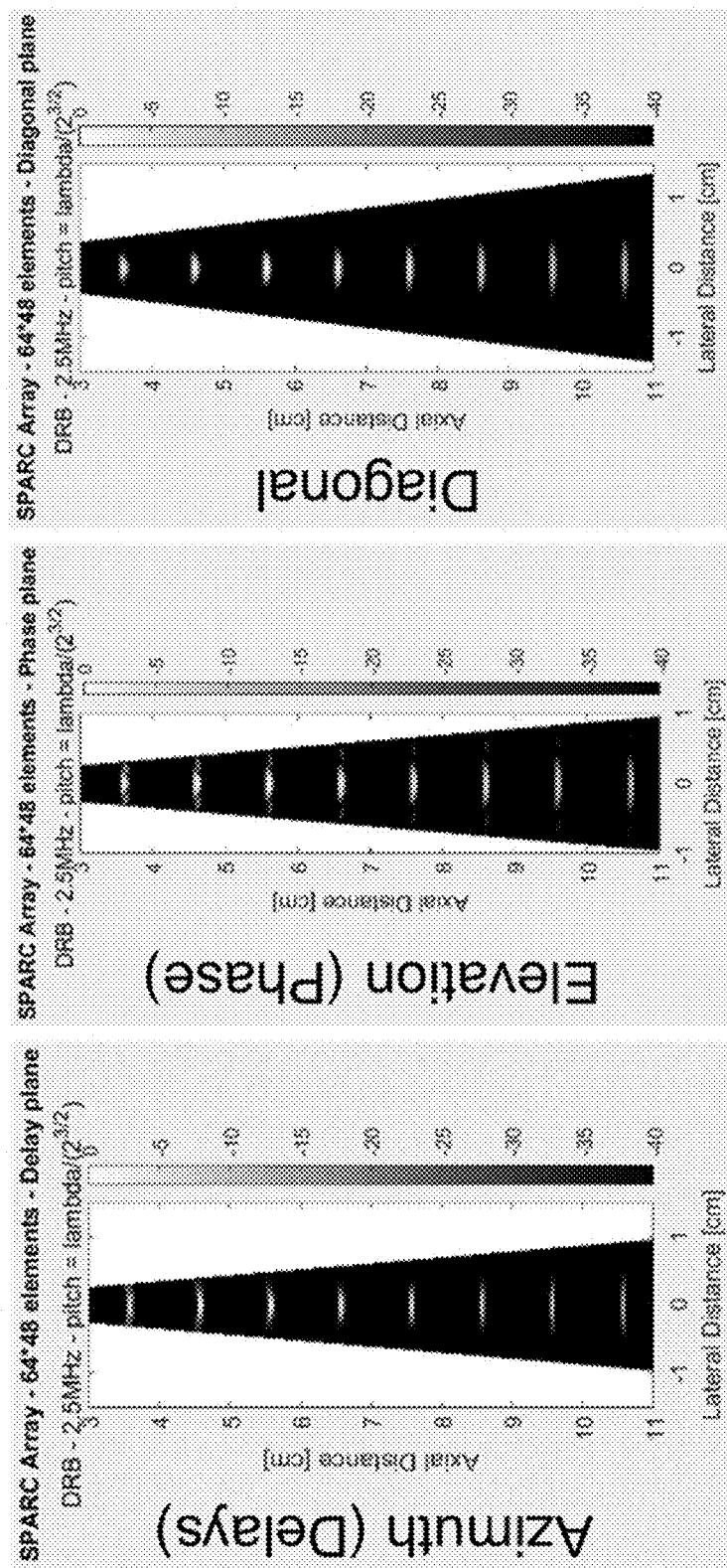
FIG. 25A, 25B, 25C show the PSF results for a cardiac array steered in the delay plane, the phase plane, and the diagonal plane.

Referring to FIG. 25A-25F, the PSF's for a cardiac array are shown, where FIG. 25A, 25B, 25C depict imaging obtained with dynamic receive beamforming (DRB) and FIG. 25D, 25E, 25F depict imaging obtained with DRB. In each image there 8 points, each spaced 10 mm apart from 35 mm to 105 mm. a, and d shows the diagonal plane (where phase steering is equal to delay steering), b and e show the phase plane, and c and f show the delay plane.

As can be seen in FIG. 25A-35F, the dynamic receive-beamforming resulted in improved lateral resolution. The improvement was most significant close to the array or much further away. These results were expected.

To determine the cardiac SPARC array's cyst imaging capabilities, a phantom with a high and low scattering region was developed, each a 5 mm diameter sphere. The results from the cardiac SPARC array were compared to an idealized 64×48 element fully wired array. The array had standard square shaped elements and a pitch of $\lambda/2$. This gave it the same dimensions as the cardiac SPARC array. To increase simulation speed and make the comparisons as one to one as possible, dynamic receive beamforming was turned off and the additional Hanning apodization from the SPARC array was removed.

Figures 26A, 26B, 26C:
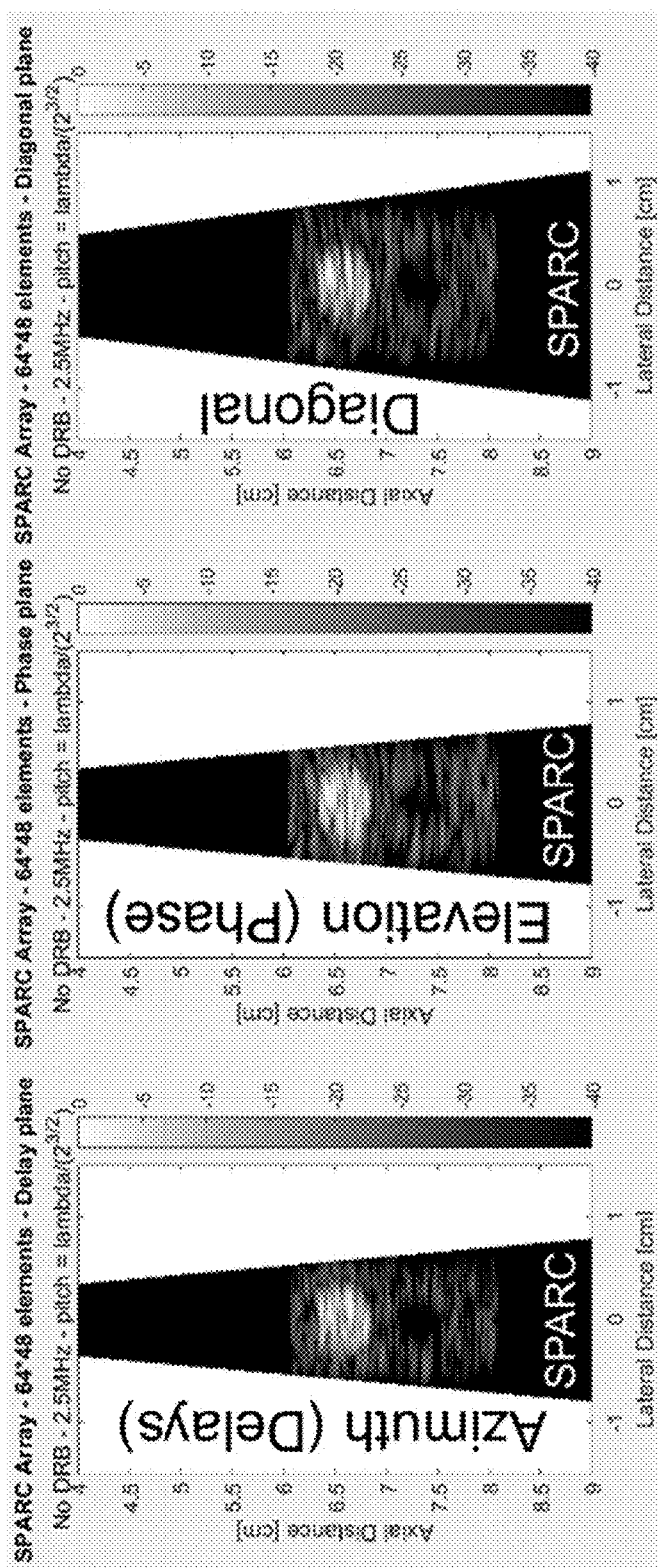
FIG. 26A, 26B, 26C show the PSF results of imaging a 4000-scatter cyst phantom with a SPARC array.
Figures 26D, 26E, 26F:
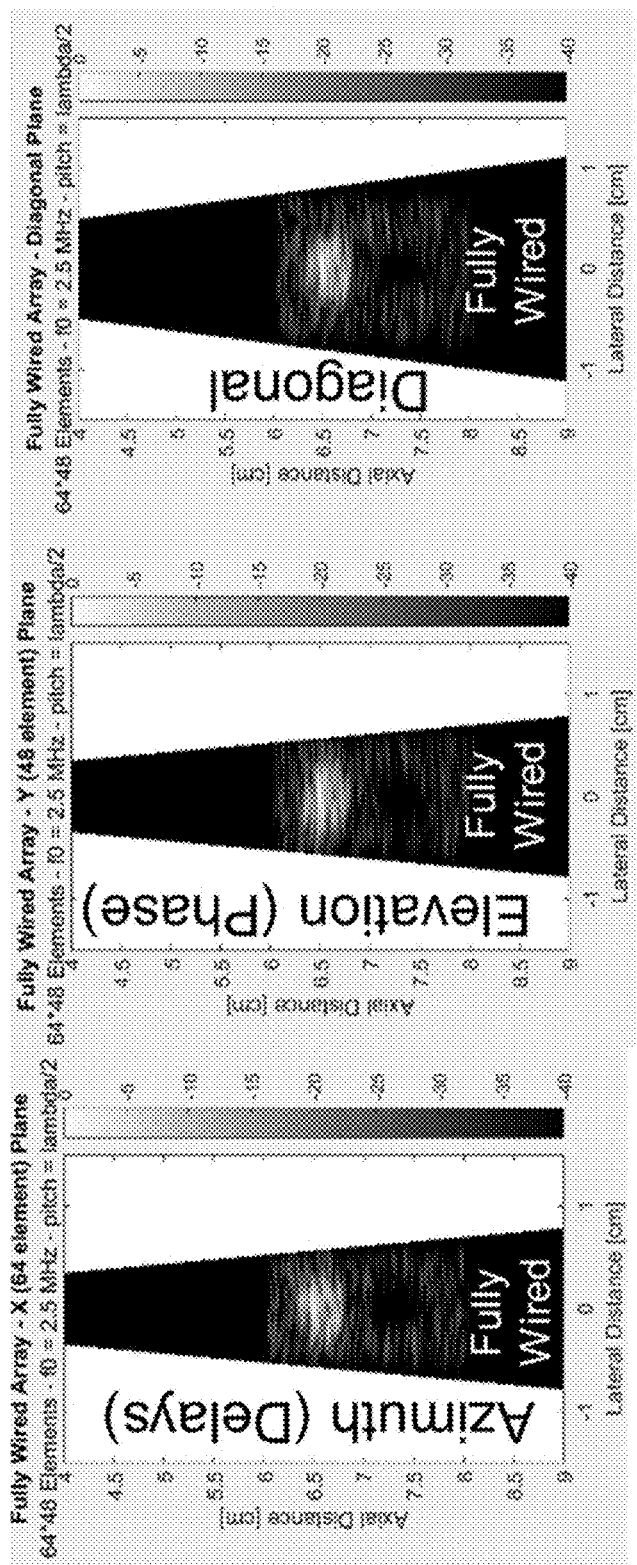
FIG. 26D, 26E, 26F show the PSF results of imaging a 4000-scatter cyst phantom with a fully wired array.

Referring to FIG. 26A-26F, the results of imaging a 4000-scatter cyst phantom with different transducers is shown, where FIG. 26A, 26B, 26C were imaged with a SPARC array and FIG. 26D, 26E, 26F are imaged with a fully wired array. As can be seen from FIG. 10, the results from the SPARC array and the fully wired array are extremely similar. The axial resolution of the SPARC arrays is not as good as the fully wired array but, otherwise they seem to be almost identical. This suggests that if the arrays can be fabricated, 3D imaging comparable to a fully wired array would be possible with SPARC arrays. This also means that the selection of any plane—including custom non-linear planes—would be possible. All of which would greatly improve the practical application of wearable ultrasound technology.

In this patent document, the word "comprising" is used in its non-limiting sense to mean that items following the word are included, but items not specifically mentioned are not excluded. A reference to an element by the indefinite article "a" does not exclude the possibility that more than one of the elements is present, unless the context requires that there be one and only one of the elements.

The scope of the following claims should not be limited by the preferred embodiments set forth in the examples above and in the drawings but should be given the broadest interpretation consistent with the description as a whole.

What is claimed is:

1. An ultrasound array system, comprising:
   an array of transducer elements made from bias-sensitive material, each transducer element comprising at least a first sub-element and a second sub-element;
   a series of column electrodes patterned in columns on a first surface of the array of transducer elements;
   a series of row electrodes patterned in rows on a second surface of the array, the rows being at an angle relative to the columns, wherein, for each transducer element, the first sub-element and the second sub-element are connected to different row electrodes; and
   a controller connected to selectively apply voltage signals to the series of column electrodes and the series of row electrodes, wherein the controller is programmed to apply a first voltage signal to the first sub-element and a second voltage signal to the second sub-element that is distinct from the first voltage signal.

2. The ultrasound array system of claim 1 wherein, for each element, the first sub-element and the second sub-element are connected to different columns.

3. The ultrasound array system of claim 1, wherein the controller further comprises receiving electronics and a processor for reconstructing images.

4. The ultrasound array system of claim 1 wherein the transducer elements comprise bias-sensitive ultrasonic elements that comprise electrostrictive material, relaxor ferroelectric material, piezoelectric material, capacitive micromachined ultrasound transducers, or combinations thereof.

5. The ultrasound array system of claim 1, wherein the array further comprises a backing layer, one or more matching layers, an acoustic lens, an interposing layer, an electromagnetic shielding layer, or combinations thereof.

6. The ultrasound array system of claim 1, wherein the controller comprises driving circuits and biasing circuits connected to the series of row electrodes, the series of column electrodes, or the series of row electrodes and the series of column electrodes.

7. The ultrasound array system of claim 1, wherein the controller applies a first driving signal to a plurality of first sub-elements and a second driving signal to a plurality of second sub-elements, the first driving signal being separated from the second driving signal by a phase shift or delay.

8. The ultrasound array system of claim 7, wherein the first driving signal is out of phase with the second driving signal by between 85 and 95 degrees.

9. The ultrasound array system of claim 1, wherein the controller is programmed to interchange a bias voltage and a driving signal between the series of column electrodes and the series of row electrodes after an initial transmit event.

10. The ultrasound array system of claim 1, wherein the controller is programmed to apply a first bias voltage pattern for a transmit event and a second bias voltage pattern for a receive event immediately following the transmit event.

11. The ultrasound array system of claim 1, wherein the controller comprises biasing electronics that comprise programmable levels, high-voltage transistors, digital to analog converters, programmable variable resistors, DC-to-DC converters, pulse-wave modulation electronics, or combinations thereof.

12. The ultrasound array system of claim 1, wherein the controller comprises one or more GPU, one or more CPU, one or more FPGA, one or more ASIC, or combination thereof.

13. The ultrasound array system of claim 1, comprising a housing having a form factor that is planar, concave, convex, plano-concave, plano-convex, biconcave, handheld, wearable, trans-esophageal, transrectal, transvaginal, endoscopic or laparoscopic.

14. The ultrasound array system of claim 1, wherein the controller is configured to implement one or more of the following imaging methods: FORCES, uFORCES, Hadamard-Encoded reception, Hadamard-Encoded X-Power Doppler, or SAFE compounding imaging.

15. The ultrasound array system of claim 1, wherein the pitch between elements is less than twice an acoustic wavelength of a center frequency of the array of transducer elements.

16. The ultrasound array system of claim 1, wherein the sub-elements have different resonance frequencies such that the array of transducer elements comprises interlaced high- and low-frequency transducer elements.

* * * * *